US009663769B2

(12) United States Patent
Greif et al.

(10) Patent No.: US 9,663,769 B2
(45) Date of Patent: May 30, 2017

(54) T7 RNA POLYMERASE VARIANTS WITH CYSTEINE-SERINE SUBSTITUTIONS

(71) Applicant: Roche Diagnostics Operations, Inc., Indianapolis, IN (US)

(72) Inventors: Michael Greif, Penzberg (DE); Christian Rudolph, Penzberg (DE); Manfred Schmidt, Penzberg (DE); Harald Sobek, Biberach (DE); Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/872,392

(22) Filed: Oct. 1, 2015

(65) Prior Publication Data

US 2016/0010069 A1 Jan. 14, 2016

Related U.S. Application Data

(63) Continuation of application No. 13/436,110, filed on Mar. 30, 2012, now abandoned.

(30) Foreign Application Priority Data

Apr. 1, 2011 (EP) .................................. 11160799

(51) Int. Cl.
*C12N 9/12* (2006.01)
(52) U.S. Cl.
CPC .... *C12N 9/1247* (2013.01); *C12Y 207/07006* (2013.01)
(58) Field of Classification Search
None
See application file for complete search history.

(56) References Cited

U.S. PATENT DOCUMENTS

| 4,952,496 A | 8/1990 | Studier et al. |
| 2007/0172861 A1 | 7/2007 | Hardin et al. |

FOREIGN PATENT DOCUMENTS

WO 2009/021191 A3 2/2009

OTHER PUBLICATIONS

European Search Report issued Sep. 20, 2011 in Application No. EP 11160799.0, 13 pages.
Bonner, Gary et al., "Characterization of a Set of T7 RNA Polymerase Active Site Mutants," The Journal of Biological Chemistry, Oct. 7, 1994, pp. 25120-25128, vol. 269, No. 40.
Brieba, Luis G. et al., "Scanning Mutagenesis Reveals Roles for Helix N of the Bacteriophage T7 RNA Polymerase Thumb Subdomain in Transcription Complex Stability, Pausing, and Termination," The Journal of Biological Chemistry, Mar. 30, 2001, pp. 10306-10313, vol. 276, No. 13.
Bujard, Hermann et al., "[26] A T5 Promoter-Based Transcription-Translation System for the Analysis of Proteins in Vitro and in Vivo," Methods in Enzymology, 1987, pp. 416-433, vol. 155.
Cheetham, Graham M. T. et al., "Structural basis for initiation of transcription from an RNA polymerase-promoter complex," Nature, May 6, 1999, pp. 80-83, vol. 399.
Creighton, Thomas E. et al., "Mechanisms and catalysts of disulphide bond formation in proteins," Trends in Biotechnology, 1995, pp. 18-23, vol. 13.
Durniak, Kimberly J. et al., "The Structure of a Transcribing T7 RNA Polymerase in Transition from Initiation to Elongation," Science, Oct. 24, 2008, pp. 553-557, vol. 322.
Fersht, Alan R. and Serrano, Luis, "Principles of protein stability derived from protein engineering experiments," Current Opinion in Structural Biology, 1993, pp. 75-83, vol. 3.
Greiner, Douglas P. et al., "Synthesis of the Protein Cutting Reagent Iron (S)-1-(p-Bromoacetamidobenzyl) ethylenediaminetetraacetate and Conjugation to Cysteine Side Chains," Bioconjugate Chemistry, 1997, pp. 44-48, vol. 8.
Guillerez, Jean et al., "A mutation in T7 RNA polymerase that facilitates promoter clearance," Proceedings of the National Academy of Sciences, Apr. 26, 2005, pp. 5958-5963, vol. 102, No. 17.
He, Biao et al., "A Mutant T7 RNA Polymerase that is Defective in RNA Binding and Blocked in the Early Stages of Transcription," Journal of Molecular Biology, 1997, pp. 275-288, vol. 265.
He, Biao et al., "Rapid Mutagenesis and Purification of Phage RNA Polymerases," Protein Expression and Purification, 1997, pp. 142-151, vol. 9.
Hénaut, A. and Danchin, A., "Analysis and Predictions from *Escherichia coli* Sequences, or *E. coli* in Silico," *Escherichia coli* and *Salmonella*, 1996, pp. 2047-2066, vol. 2, Ch. 114.
Jeruzalmi, David and Steitz, Thomas A., "Structure of T7 RNA polymerase complexed to the transcriptional inhibitor T7 lysozyme," The EMBO Journal, 1998, pp. 4101-4113, vol. 17, No. 14.
Jeruzalmi, David and Steitz, Thomas A., "Use of Organic Cosmotropic Solutes to Crystallize Flexible Proteins: Application to T7 RNA Polymerase and its Complex with the Inhibitor T7 Lysozyme," Journal of Molecular Biology, 1997, pp. 746-756, vol. 274.
King, Garry C. et al., "Transcription by T7 RNA Polymerase Is Not Zinc-Dependent and Is Abolished on Amidomethylation of Cysteine-347," Biochemistry, 1986, pp. 36-40, vol. 25.
Kopetzki, Erhard et al., "Control of formation of active soluble or inactive insoluble baker's yeast α-glucosidase PI in *Escherichia coli* by induction and growth conditions," Mol. Gen. Genet., 1989, pp. 149-155, vol. 216.

(Continued)

*Primary Examiner* — Richard Hutson
(74) *Attorney, Agent, or Firm* — Roche Diagnostics Operations, Inc.

(57) ABSTRACT

The present disclosure provide novel variants of T7 RNA polymerase. Embodiments of T7 variants, according to the instant invention, include a Cysteine-Serine substitution on position 723 of the amino acid sequence of the T7 polypeptide. Embodiments of T7 variants according to the instant invention have a DNA-dependent RNA polymerase enzymatic activity and a reduced tendency to form intramolecular homodimers by way of oxidizing thiol groups. The amino acid substitutions within the T7 variants disclosed herein impact minimally, if at all, the RNA polymerase activity of the T7 polypeptide. Further, the mutations of the disclosed embodiments may optionally be combined with mutations which provide enhanced thermostability compared to the wild-type reference.

5 Claims, 3 Drawing Sheets

(56) References Cited

OTHER PUBLICATIONS

Lee, Byungkook and Vasmatzis, George, "Stabilization of protein structures," Current Opinion in Biotechnology, 1997, pp. 423-428, vol. 8.

Ma, Kalyu et al., "Probing conformational changes in T7 RNA polymerase during initiation and termination by using engineered disulfide linkages," Proceedings of the National Academy of Sciences, Dec. 6, 2005, pp. 17612-17617, vol. 102, No. 49.

Milligan, John F. et al., "Oligribonucleotide synthesis using T7 RNA polymerase and synthetic DNA templates," Nucleic Acids Research, 1987, pp. 8783-8798, vol. 15, No. 21.

Mukherjee, Srabani et al., "Structural Transitions Mediating Transcription Initiation by T7 RNA Polymerase," Cell, Jul. 12, 2002, pp. 81-91, vol. 110.

Nayak, Dhananjaya et al., "Functional Architecture of T7 RNA Polymerase Transcription Complexes," Journal of Molecular Biology, 2007, pp. 490-500, vol. 371.

Ngo, J. Thomas et al., "Computational Complexity, Protein Structure Prediction, and the Levinthal Paradox," The Protein Folding Problem and Tertiary Structure Prediction, 1994, pp. 433 and 492-495, Ch. 14, Merz et al. (ed.), Birkhauser, Boston, MA.

Sambrook, Joseph and Russell, David W., Molecular Cloning a Laboratory Manual Third Edition, 2001, vols. 1-3, Cold Spring Harbour Laboratory Press, Cold Spring Harbour, New York.

Senthikumar, Velusamy et al., "Serine substitution of for cysteine residues in levansucrase selectively abolishes levan forming activity," Biotechnology Letters, 2003, pp. 1653-1656, vol. 25.

Sousa, Rui and Mukherjee, Srabani, "T7 RNA Polymerase," Progress in Nucleic Acid Research and Molecular Biology, 2003, pp. 1-41, vol. 73.

Steitz, Thomas A., "The structural changes of T7 RNA polymerase from transcription initiation to elongation," Current Opinion in Structural Biology, 2009, pp. 683-690, vol. 19.

Studier, F. William and Moffatt, Barbara A., "Use of Bacteriophage T7 RNA Polymerase to Direct Selective High-level Expression of Cloned Genes," Journal of Molecular Biology, 1986, pp. 113-130, vol. 189.

Temiakov, Dmitry et al., "Structural Basis for Substrate Selection by T7 RNA Polymerase," Cell, Feb. 6, 2004, pp. 381-391, vol. 116.

Van Den Brulle, Jan et al., "A novel solid phase technology for high-throughput gene synthesis," BioTechniques, 2008, pp. 340-343, vol. 45, No. 3.

Winter, Greg et al., "Redesigning enzyme structure by site-directed mutagenesis: tyrosyl tRNA synthetase and ATP binding," Nature, Oct. 21, 1982, pp. 756-758, vol. 299.

Yin, Y. Whitney and Steitz, Thomas A., "The Structural Mechanism of Translocation and Helicase Activity in T7 RNA Polymerase," Cell, Feb. 6, 2004, pp. 393-404, vol. 116.

Zlatanova, Jordanka et al., "Single-Molecule Approaches Reveal the Idiosyncrasies of RNA Polymerases," Structure, Jun. 2006, pp. 953-966, vol. 14.

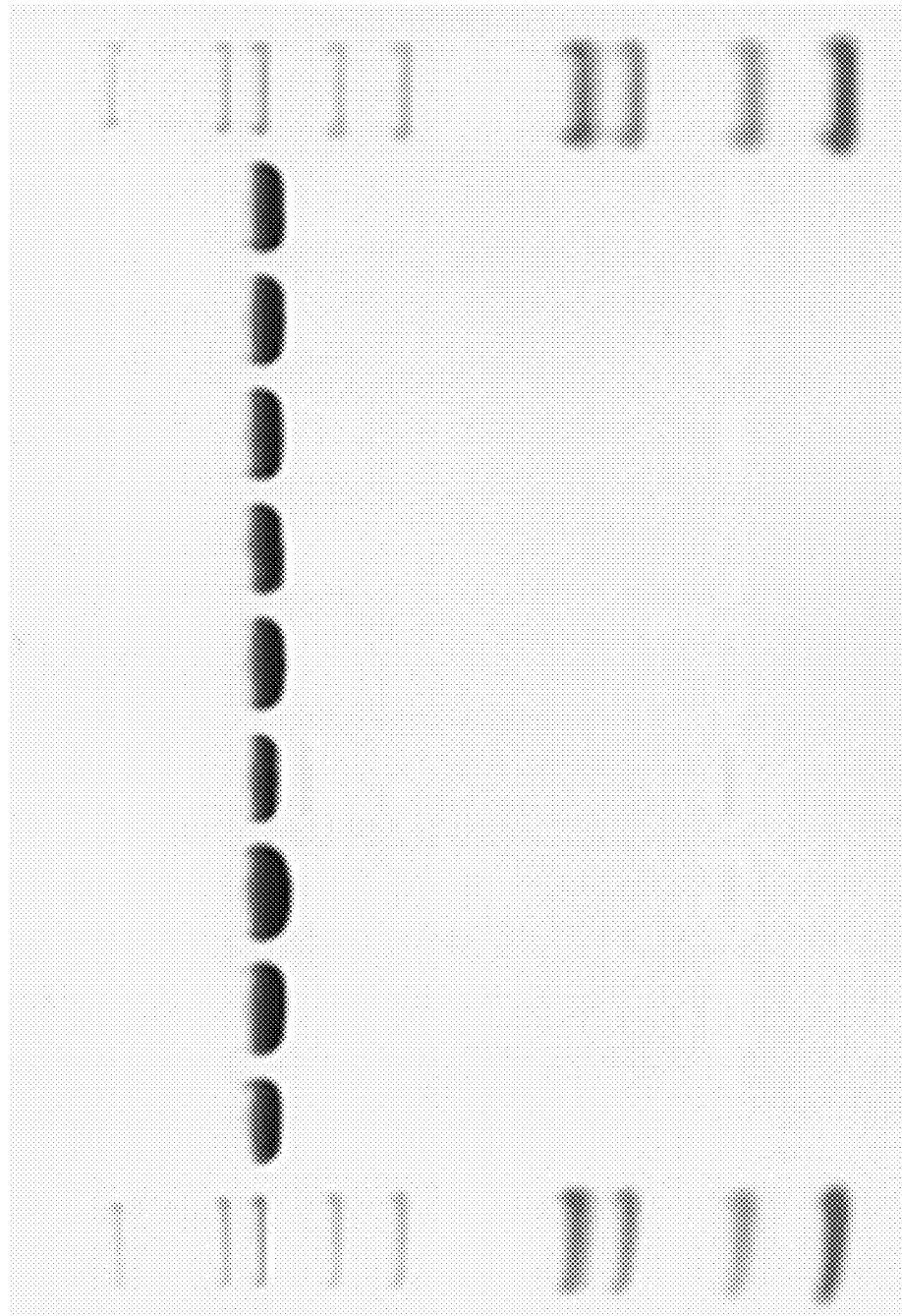

SEQUENCE LISTING

```
<160> NUMBER OF SEQ ID NOS: 76

<210> SEQ ID NO 1
<211> LENGTH: 2655
<212> TYPE: DNA
<213> ORGANISM: Escherichia coli
<220> FEATURE:
<221> NAME/KEY: misc_feature
<222> LOCATION: (1)..(2655)
<223> OTHER INFORMATION: DNA sequence encoding wild-type T7 DNA-
      dependent RNA polymerase, including start codon encoding
      N-terminal methionine; corresponding to #1 in Table 3

<400> SEQUENCE: 1
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctc agcaagattc tccgttctgc ttccttgcgt tctgctttga gtacgctggg    1560
gtacagcacc acggcctgag ctataactgc tcccttccgc tggcgtttga cgggtcttgc    1620
```

-continued

```
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg     1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 2
<211> LENGTH: 883
<212> TYPE: PRT
<213> ORGANISM: Escherichia coli
<220> FEATURE:
<221> NAME/KEY: MISC_FEATURE
<222> LOCATION: (1)..(883)
<223> OTHER INFORMATION: wild-type T7 DNA-dependent RNA polymerase,
      amino acid sequence including N-terminal methionine;
      corresponding to #1 in Table 3

<400> SEQUENCE: 2

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160
```

-continued

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

| | | | | | | | | | | | | |
|---|---|---|---|---|---|---|---|---|---|---|---|---|
| Lys | Val | Asn | Glu | Ile | Leu | Gln | Ala | Asp | Ala | Ile | Asn | Gly | Thr | Asp | Asn |
| | | | 580 | | | | 585 | | | | 590 | | | | |

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

```
<210> SEQ ID NO 3
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys125Ser variant of
      T7 DNA-dependent RNA polymerase, including start codon encoding
      N-terminal methionine; corresponding to #2 in Table 3

<400> SEQUENCE: 3
```
atgaacacga ttaacatcgc taagaacgac ttctctgaca tcgaactggc tgctatcccg    60
ttcaacactc tggctgacca ttacggtgag cgtttagctc gcgaacagtt ggcccttgag   120

-continued

```
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg ctagcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttgga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga cgcatcaag    1440
ttcattgagg aaaaccacga aacatcatg gcttgcgcta gtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
```

-continued

```
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 4
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys125Ser variant of T7 DNA-dependent RNA polymerase, amino acid sequence including N-terminal methionine; corresponding to #2 in Table 3

<400> SEQUENCE: 4

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Ser Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300
```

```
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720
```

```
Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 5
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys347Ser variant of
      T7 DNA-dependent RNA polymerase, including start codon encoding
      N-terminal methionine; corresponding to #3 in Table 3

<400> SEQUENCE: 5
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga gtttgagcg tcaacttaaa      180 gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa      540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
```

```
aacattgcgc aaaacaccgc atggaaaatc aacaagaaag tcctagcggt cgccaacgta    1020
atcaccaagt ggaagcatag cccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgtttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga cgcatcaag    1440 ttcattgagg aaaaccacga gaacatcatg gcttgcgcta gtctccact ggagaacact    1500 tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 6  
<211> LENGTH: 883  
<212> TYPE: PRT  
<213> ORGANISM: Artificial Sequence  
<220> FEATURE:  
<223> OTHER INFORMATION: Synthetic variant polypeptide  
<220> FEATURE:  
<221> NAME/KEY: MISC_FEATURE  
<222> LOCATION: (1)..(883)  
<223> OTHER INFORMATION: Cys347Servariant of T7 DNA-dependent RNA
      polymerase, amino acid sequence including N-terminal methionine;
      corresponding to #3 in Table 3

<400> SEQUENCE: 6

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu

-continued

```
                20                  25                  30
Ala Arg Glu Gln Leu Ala Leu Glu His Glu Ser Tyr Glu Met Gly Glu
             35                  40                  45
Ala Arg Phe Arg Lys Met Phe Glu Arg Gln Leu Lys Ala Gly Glu Val
 50                  55                  60
Ala Asp Asn Ala Ala Lys Pro Leu Ile Thr Thr Leu Leu Pro Lys
 65                  70                  75                  80
Met Ile Ala Arg Ile Asn Asp Trp Phe Glu Glu Val Lys Ala Lys Arg
                 85                  90                  95
Gly Lys Arg Pro Thr Ala Phe Gln Phe Leu Gln Glu Ile Lys Pro Glu
            100                 105                 110
Ala Val Ala Tyr Ile Thr Ile Lys Thr Thr Leu Ala Cys Leu Thr Ser
            115                 120                 125
Ala Asp Asn Thr Thr Val Gln Ala Val Ala Ser Ala Ile Gly Arg Ala
            130                 135                 140
Ile Glu Asp Glu Ala Arg Phe Gly Arg Ile Arg Asp Leu Glu Ala Lys
145                 150                 155                 160
His Phe Lys Lys Asn Val Glu Gln Leu Asn Lys Arg Val Gly His
             165                 170                 175
Val Tyr Lys Lys Ala Phe Met Gln Val Val Glu Ala Asp Met Leu Ser
             180                 185                 190
Lys Gly Leu Leu Gly Glu Ala Trp Ser Ser Trp His Lys Glu Asp
             195                 200                 205
Ser Ile His Val Gly Val Arg Cys Ile Glu Met Leu Ile Glu Ser Thr
             210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
             245                 250                 255
Arg Ala Gly Ala Leu Ala Gly Ile Ser Pro Met Phe Gln Pro Cys Val
             260                 265                 270
Val Pro Pro Lys Pro Trp Thr Gly Ile Thr Gly Gly Tyr Trp Ala
             275                 280                 285
Asn Gly Arg Arg Pro Leu Ala Leu Val Arg Thr His Ser Lys Lys Ala
             290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
             325                 330                 335
Val Ala Asn Val Ile Thr Lys Trp Lys His Ser Pro Val Glu Asp Ile
             340                 345                 350
Pro Ala Ile Glu Arg Glu Glu Leu Pro Met Lys Pro Glu Asp Ile Asp
             355                 360                 365
Met Asn Pro Glu Ala Leu Thr Ala Trp Lys Arg Ala Ala Ala Val
             370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
             405                 410                 415
Pro Tyr Asn Met Asp Trp Arg Gly Arg Val Tyr Ala Val Ser Met Phe
             420                 425                 430
Asn Pro Gln Gly Asn Asp Met Thr Lys Gly Leu Leu Thr Leu Ala Lys
             435                 440                 445
```

```
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His Gly Leu Ser Tyr
        515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
                820                 825                 830
Val Asp Thr Tyr Glu Ser Cys Asp Val Leu Ala Asp Phe Tyr Asp Gln
            835                 840                 845
Phe Ala Asp Gln Leu His Glu Ser Gln Leu Asp Lys Met Pro Ala Leu
    850                 855                 860
```

Pro Ala Lys Gly Asn Leu Asn Leu Arg Asp Ile Leu Glu Ser Asp Phe
865                 870                 875                 880

Ala Phe Ala

<210> SEQ ID NO 7
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys492Ser variant of
      T7 DNA-dependent RNA polymerase, including start codon encoding
      N-terminal methionine; corresponding to #4 in Table 3

<400> SEQUENCE: 7
atgaacacga ttaacatcgc taagaacgac ttctctgaca tcgaactggc tgctatcccg     60
ttcaacactc tggctgacca ttacggtgag cgtttagctc gcaacagtt ggcccttgag    120 catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg aaacgtgct   1140 gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaggtaaa ccaatcggta aggaaggtta ctactggctg   1380
aaaatccacg gtgcaaactg tgcgggtgtc gataaggttc cgttccctga gcgcatcaag   1440
ttcattgagg aaaccacga gaacatcatg gctagcgcta gtctccact ggagaacact   1500 tggtgggctc agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740

-continued

```
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                      2655
```

<210> SEQ ID NO 8
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys492Ser variant of T7 DNA-dependent RNA
      polymerase, amino acid sequence including N-terminal methionine;
      corresponding to #4 in Table 3

<400> SEQUENCE: 8

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
```

```
            165                 170                 175
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Ser Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590
```

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 9
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys515Ser variant of
      T7 DNA-dependent RNA polymerase, including start codon encoding
      N-terminal methionine; corresponding to #5 in Table 3

<400> SEQUENCE: 9
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa    180

-continued

```
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tcagctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg tgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta gctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
```

```
atgccagcac ttccggctaa aggtaacttg aacctccgtg acatcttaga gtcggacttc    2640
gcgttcgcgt aataa                                                     2655
```

<210> SEQ ID NO 10
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys515Ser variant of T7 DNA-dependent RNA
      polymerase, amino acid sequence including N-terminal methionine;
      corresponding to #5 in Table 3

<400> SEQUENCE: 10

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
```

```
            305                 310                 315                 320

Asn Ile Ala Gln Asn Thr Ala Trp Lys Ile Asn Lys Lys Val Leu Ala
                        325                 330                 335

Val Ala Asn Val Ile Thr Lys Trp Lys His Cys Pro Val Glu Asp Ile
                        340                 345                 350

Pro Ala Ile Glu Arg Glu Glu Leu Pro Met Lys Pro Glu Asp Ile Asp
                        355                 360                 365

Met Asn Pro Glu Ala Leu Thr Ala Trp Lys Arg Ala Ala Ala Val
            370                 375                 380

Tyr Arg Lys Asp Lys Ala Arg Lys Ser Arg Ile Ser Leu Glu Phe
        385                 390                 395                 400

Met Leu Glu Gln Ala Asn Lys Phe Ala Asn His Lys Ala Ile Trp Phe
                        405                 410                 415

Pro Tyr Asn Met Asp Trp Arg Gly Arg Val Tyr Ala Val Ser Met Phe
                        420                 425                 430

Asn Pro Gln Gly Asn Asp Met Thr Lys Gly Leu Leu Thr Leu Ala Lys
                        435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
        465                 470                 475                 480

Phe Ile Glu Glu Asn His Glu Asn Ile Met Ala Cys Ala Lys Ser Pro
                        485                 490                 495

Leu Glu Asn Thr Trp Trp Ala Glu Gln Asp Ser Pro Phe Cys Phe Leu
                        500                 505                 510

Ala Phe Ser Phe Glu Tyr Ala Gly Val Gln His His Gly Leu Ser Tyr
                        515                 520                 525

Asn Cys Ser Leu Pro Leu Ala Phe Asp Gly Ser Cys Ser Gly Ile Gln
                        530                 535                 540

His Phe Ser Ala Met Leu Arg Asp Glu Val Gly Gly Arg Ala Val Asn
        545                 550                 555                 560

Leu Leu Pro Ser Glu Thr Val Gln Asp Ile Tyr Gly Ile Val Ala Lys
                        565                 570                 575

Lys Val Asn Glu Ile Leu Gln Ala Asp Ala Ile Asn Gly Thr Asp Asn
                        580                 585                 590

Glu Val Val Thr Val Thr Asp Glu Asn Thr Gly Glu Ile Ser Glu Lys
                        595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
        625                 630                 635                 640

Ser Lys Glu Phe Gly Phe Arg Gln Gln Val Leu Glu Asp Thr Ile Gln
                        645                 650                 655

Pro Ala Ile Asp Ser Gly Lys Gly Leu Met Phe Thr Gln Pro Asn Gln
                        660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
                        690                 695                 700

Leu Leu Ala Ala Glu Val Lys Asp Lys Lys Thr Gly Glu Ile Leu Arg
        705                 710                 715                 720

Lys Arg Cys Ala Val His Trp Val Thr Pro Asp Gly Phe Pro Val Trp
                        725                 730                 735
```

```
Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                    820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 11
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser variant of
      T7 DNA-dependent RNA polymerase, including start codon encoding
      N-terminal methionine; corresponding to #6 in Table 3

<400> SEQUENCE: 11

```
atgaacacga ttaacatcgc taagaacgac ttctctgaca tcgaactggc tgctatcccg    60
ttcaacactc tggctgacca ttacggtgag cgtttagctc gcaacagtt ggcccttgag    120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggg ccattgagga cgaggctcgc ttcggtcgta ccgtgaccct gaagctaag    480
cacttcaaga aaacgttga ggaacaactc aacaagcgcg tagggcacgt ctacaagaaa   540
gcatttatgc aagttgtcga ggctgacatg ctctctaagg tctactcgg tggcgaggcg    600
tggtcttcgt ggcataagga agactctatt catgtaggag tacgctgcat cgagatgctc   660
attgagtcaa ccggaatggt tagcttacac cgccaaaatg ctggcgtagt aggtcaagac   720
tctgagacta cgaactcgc acctgaatac gctgaggcta cgcaacccg tgcaggtgcg    780
ctggctggca tctctccgat gttccaacct tgcgtagttc ctcctaagcc gtggactggc   840
attactggtg gtggctattg ggctaacggt cgtcgtcctc tggcgctggt gcgtactcac   900
agtaagaaag cactgatgcg ctacgaagac gtttacatgc ctgaggtgta caaagcgatt   960
aacattgcgc aaaacaccgc atggaaaatc aacaagaaag tcctagcggt cgccaacgta  1020
```

```
atcaccaagt ggaagcattg tccggtcgag acatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgttta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                   2655
```

<210> SEQ ID NO 12
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser variant of T7 DNA-dependent RNA
      polymerase, amino acid sequence including N-terminal methionine;
      corresponding to #6 in Table 3

<400> SEQUENCE: 12

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

-continued

```
Ala Arg Glu Gln Leu Ala Leu Glu His Glu Ser Tyr Glu Met Gly Glu
         35                  40                  45
Ala Arg Phe Arg Lys Met Phe Glu Arg Gln Leu Lys Ala Gly Glu Val
 50                  55                  60
Ala Asp Asn Ala Ala Lys Pro Leu Ile Thr Thr Leu Leu Pro Lys
 65                  70                  75                  80
Met Ile Ala Arg Ile Asn Asp Trp Phe Glu Val Lys Ala Lys Arg
                 85                  90                  95
Gly Lys Arg Pro Thr Ala Phe Gln Phe Leu Gln Glu Ile Lys Pro Glu
                100                 105                 110
Ala Val Ala Tyr Ile Thr Ile Lys Thr Thr Leu Ala Cys Leu Thr Ser
             115                 120                 125
Ala Asp Asn Thr Thr Val Gln Ala Val Ala Ser Ala Ile Gly Arg Ala
         130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Gly Tyr Trp Ala
        275                 280                 285
Asn Gly Arg Arg Pro Leu Ala Leu Val Arg Thr His Ser Lys Lys Ala
    290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
        355                 360                 365
Met Asn Pro Glu Ala Leu Thr Ala Trp Lys Arg Ala Ala Ala Val
    370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
```

```
            450             455             460
Ala Asn Cys Ala Gly Val Asp Lys Val Pro Phe Pro Glu Arg Ile Lys
465                 470             475                 480

Phe Ile Glu Glu Asn His Glu Asn Ile Met Ala Cys Ala Lys Ser Pro
                485             490                 495

Leu Glu Asn Thr Trp Trp Ala Glu Gln Asp Ser Pro Phe Cys Phe Leu
            500             505             510

Ala Phe Cys Phe Glu Tyr Ala Gly Val Gln His His Gly Leu Ser Tyr
        515             520             525

Asn Cys Ser Leu Pro Leu Ala Phe Asp Gly Ser Cys Ser Gly Ile Gln
    530             535             540

His Phe Ser Ala Met Leu Arg Asp Glu Val Gly Gly Arg Ala Val Asn
545             550             555                 560

Leu Leu Pro Ser Glu Thr Val Gln Asp Ile Tyr Gly Ile Val Ala Lys
                565             570             575

Lys Val Asn Glu Ile Leu Gln Ala Asp Ala Ile Asn Gly Thr Asp Asn
            580             585             590

Glu Val Val Thr Val Thr Asp Glu Asn Thr Gly Glu Ile Ser Glu Lys
        595             600             605

Val Lys Leu Gly Thr Lys Ala Leu Ala Gly Gln Trp Leu Ala Tyr Gly
    610             615             620

Val Thr Arg Ser Val Thr Lys Arg Ser Val Met Thr Leu Ala Tyr Gly
625             630             635             640

Ser Lys Glu Phe Gly Phe Arg Gln Gln Val Leu Glu Asp Thr Ile Gln
                645             650             655

Pro Ala Ile Asp Ser Gly Lys Gly Leu Met Phe Thr Gln Pro Asn Gln
            660             665             670

Ala Ala Gly Tyr Met Ala Lys Leu Ile Trp Glu Ser Val Ser Val Thr
        675             680             685

Val Val Ala Ala Val Glu Ala Met Asn Trp Leu Lys Ser Ala Ala Lys
    690             695             700

Leu Leu Ala Ala Glu Val Lys Asp Lys Lys Thr Gly Glu Ile Leu Arg
705             710             715                 720

Lys Arg Ser Ala Val His Trp Val Thr Pro Asp Gly Phe Pro Val Trp
                725             730             735

Gln Glu Tyr Lys Lys Pro Ile Gln Thr Arg Leu Asn Leu Met Phe Leu
            740             745             750

Gly Gln Phe Arg Leu Gln Pro Thr Ile Asn Thr Asn Lys Asp Ser Glu
        755             760             765

Ile Asp Ala His Lys Gln Glu Ser Gly Ile Ala Pro Asn Phe Val His
    770             775             780

Ser Gln Asp Gly Ser His Leu Arg Lys Thr Val Trp Ala His Glu
785             790             795                 800

Lys Tyr Gly Ile Glu Ser Phe Ala Leu Ile His Asp Ser Phe Gly Thr
                805             810             815

Ile Pro Ala Asp Ala Ala Asn Leu Phe Lys Ala Val Arg Glu Thr Met
            820             825             830

Val Asp Thr Tyr Glu Ser Cys Asp Val Leu Ala Asp Phe Tyr Asp Gln
        835             840             845

Phe Ala Asp Gln Leu His Glu Ser Gln Leu Asp Lys Met Pro Ala Leu
    850             855             860

Pro Ala Lys Gly Asn Leu Asn Leu Arg Asp Ile Leu Glu Ser Asp Phe
865             870             875             880
```

Ala Phe Ala

<210> SEQ ID NO 13
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys839Ser variant of
      T7 DNA-dependent RNA polymerase, including start codon encoding
      N-terminal methionine; corresponding to #7 in Table 3

<400> SEQUENCE: 13

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | ctgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | gtcgtgttta | cgctgtgtca | atgttcaacc | cgcaaggtaa | cgatatgacc | 1320 |
| aaaggactgc | ttacgctggc | gaaaggtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | gaacatcatg | gcttgcgcta | agtctccact | ggagaacact | 1500 |
| tggtgggctg | agcaagattc | tccgttctgc | ttccttgcgt | tctgctttga | gtacgctggg | 1560 |
| gtacagcacc | acggcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattg | ttgctaagaa | agtcaacgag | 1740 |
| attctacaag | cagacgcaat | caatgggacc | gataacgaag | tagttaccgt | gaccgatgag | 1800 |

-continued

```
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtctagcgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 14
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys839Ser variant of T7 DNA-dependent RNA
      polymerase, amino acid sequence including N-terminal methionine;
      corresponding to #7 in Table 3

<400> SEQUENCE: 14

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

-continued

```
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
```

|   |   |   |   |   | 595 |   |   |   |   | 600 |   |   |   |   | 605 |   |

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Ser Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 15
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys125Ser, Cys347Ser,
    Cys492Ser, Cys515Ser, Cys723Ser, Cys839Servariant of T7 DNA-
    dependent RNA polymerase, including start codon encoding
    N-terminal methionine; corresponding to #8 in Table 3

<400> SEQUENCE: 15
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240

```
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg ctagcctaac cagtgctgac aatacaaccg ttcaggctgt agcaagcgca      420
atcggtcggg ccattgagga cgaggctcgc ttcggtcgta tccgtgacct tgaagctaag      480
cacttcaaga aaacgttgga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcatag cccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtgtttta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gctagcgcta agtctccact ggagaacact     1500
tggtgggctg agcaagattc tccgttctgc ttccttgcgt tcagctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga aaagtcaag ctgggcacta aggcactggc tggtcaatgg     1860
ctggcttacg gtgttactcg cagtgtgact aagcgttcag tcatgacgct ggcttacggg     1920
tccaaagagt tcgcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta agctgctggc tgctgaggtc aaagataaga agactggaga gattcttcgc     2160
aagcgtagcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca caaagataag cgagattgat gcacacaaac aggagtctgg tatcgctcct     2340
aactttgtac acagccaaga cggtagccac cttcgtaaga ctgtagtgtg gcacacgag     2400 aagtacggaa tcgaatcttt tgcactgatt cacgactcct tcggtaccat tccggctgac     2460
gctgcgaact gttcaaagc agtgcgcgaa actatggttg acacatatga gtctagcgat     2520
gtactggctg atttctacga ccagttcgct gaccagttgc acgagtctca attggacaaa     2580
```

-continued

```
atgccagcac ttccggctaa aggtaacttg aacctccgtg acatcttaga gtcggacttc    2640
gcgttcgcgt aataa                                                     2655
```

<210> SEQ ID NO 16
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys125Ser, Cys347Ser, Cys492Ser, Cys515Ser,
      Cys723Ser, Cys839Ser variant of T7 DNA-dependent RNA polymerase,
      amino acid sequence including N-terminal methionine; corresponding
      to #8 in Table 3

<400> SEQUENCE: 16

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Ser Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile

```
            305                 310                 315                 320
        Asn Ile Ala Gln Asn Thr Ala Trp Lys Ile Asn Lys Lys Val Leu Ala
                        325                 330                 335

Val Ala Asn Val Ile Thr Lys Trp Lys His Ser Pro Val Glu Asp Ile
                        340                 345                 350

Pro Ala Ile Glu Arg Glu Glu Leu Pro Met Lys Pro Glu Asp Ile Asp
                        355                 360                 365

Met Asn Pro Glu Ala Leu Thr Ala Trp Lys Arg Ala Ala Ala Ala Val
                370                 375                 380

Tyr Arg Lys Asp Lys Ala Arg Lys Ser Arg Ile Ser Leu Glu Phe
        385                 390                 395                 400

Met Leu Glu Gln Ala Asn Lys Phe Ala Asn His Lys Ala Ile Trp Phe
                        405                 410                 415

Pro Tyr Asn Met Asp Trp Arg Gly Arg Val Tyr Ala Val Ser Met Phe
                        420                 425                 430

Asn Pro Gln Gly Asn Asp Met Thr Lys Gly Leu Leu Thr Leu Ala Lys
                        435                 440                 445

Gly Lys Pro Ile Gly Lys Glu Gly Tyr Tyr Trp Leu Lys Ile His Gly
                        450                 455                 460

Ala Asn Cys Ala Gly Val Asp Lys Val Pro Phe Pro Glu Arg Ile Lys
        465                 470                 475                 480

Phe Ile Glu Glu Asn His Glu Asn Ile Met Ala Ser Ala Lys Ser Pro
                        485                 490                 495

Leu Glu Asn Thr Trp Trp Ala Glu Gln Asp Ser Pro Phe Cys Phe Leu
                        500                 505                 510

Ala Phe Ser Phe Glu Tyr Ala Gly Val Gln His His Gly Leu Ser Tyr
                        515                 520                 525

Asn Cys Ser Leu Pro Leu Ala Phe Asp Gly Ser Cys Ser Gly Ile Gln
                        530                 535                 540

His Phe Ser Ala Met Leu Arg Asp Glu Val Gly Gly Arg Ala Val Asn
        545                 550                 555                 560

Leu Leu Pro Ser Glu Thr Val Gln Asp Ile Tyr Gly Ile Val Ala Lys
                        565                 570                 575

Lys Val Asn Glu Ile Leu Gln Ala Asp Ala Ile Asn Gly Thr Asp Asn
                        580                 585                 590

Glu Val Val Thr Val Thr Asp Glu Asn Thr Gly Glu Ile Ser Glu Lys
                        595                 600                 605

Val Lys Leu Gly Thr Lys Ala Leu Ala Gly Gln Trp Leu Ala Tyr Gly
                        610                 615                 620

Val Thr Arg Ser Val Thr Lys Arg Ser Val Met Thr Leu Ala Tyr Gly
        625                 630                 635                 640

Ser Lys Glu Phe Gly Phe Arg Gln Gln Val Leu Glu Asp Thr Ile Gln
                        645                 650                 655

Pro Ala Ile Asp Ser Gly Lys Gly Leu Met Phe Thr Gln Pro Asn Gln
                        660                 665                 670

Ala Ala Gly Tyr Met Ala Lys Leu Ile Trp Glu Ser Val Ser Val Thr
                        675                 680                 685

Val Val Ala Ala Val Glu Ala Met Asn Trp Leu Lys Ser Ala Ala Lys
                        690                 695                 700

Leu Leu Ala Ala Glu Val Lys Asp Lys Lys Thr Gly Glu Ile Leu Arg
        705                 710                 715                 720

Lys Arg Ser Ala Val His Trp Val Thr Pro Asp Gly Phe Pro Val Trp
                        725                 730                 735
```

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Ser Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 17
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Leu variant of
      T7 DNA-dependent RNA polymerase, including start codon encoding
      N-terminal methionine; corresponding to #9 in Table 3

<400> SEQUENCE: 17
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct gaagctaag      480 cacttcaaga aaacgttga ggaacaactc aacaagcgcg tagggcacgt ctacaagaaa      540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta cgaactcgc acctgaatac gctgaggcta cgcaacccg tgcaggtgcg      780 ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020

```
atcaccaagt ggaagcattg tccggtcgag acatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtctgta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 18
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Leu variant of T7 DNA-dependent RNA polymerase, amino acid sequence including N-terminal methionine; corresponding to #9 in Table 3

<400> SEQUENCE: 18

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30
```

-continued

```
Ala Arg Glu Gln Leu Ala Leu Glu His Glu Ser Tyr Glu Met Gly Glu
             35                  40                  45

Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
```

```
                450             455             460
Ala Asn Cys Ala Gly Val Asp Lys Val Pro Phe Pro Glu Arg Ile Lys
465                 470             475                 480

Phe Ile Glu Glu Asn His Glu Asn Ile Met Ala Cys Ala Lys Ser Pro
                    485             490                 495

Leu Glu Asn Thr Trp Trp Ala Glu Gln Asp Ser Pro Phe Cys Phe Leu
                500             505             510

Ala Phe Cys Phe Glu Tyr Ala Gly Val Gln His His Gly Leu Ser Tyr
            515             520             525

Asn Cys Ser Leu Pro Leu Ala Phe Asp Gly Ser Cys Ser Gly Ile Gln
        530             535             540

His Phe Ser Ala Met Leu Arg Asp Glu Val Gly Gly Arg Ala Val Asn
545             550             555                 560

Leu Leu Pro Ser Glu Thr Val Gln Asp Ile Tyr Gly Ile Val Ala Lys
                565             570             575

Lys Val Asn Glu Ile Leu Gln Ala Asp Ala Ile Asn Gly Thr Asp Asn
                580             585             590

Glu Val Val Thr Val Thr Asp Glu Asn Thr Gly Glu Ile Ser Glu Lys
            595             600             605

Val Lys Leu Gly Thr Lys Ala Leu Ala Gly Gln Trp Leu Ala Tyr Gly
        610             615             620

Val Thr Arg Ser Val Thr Lys Arg Ser Val Met Thr Leu Ala Tyr Gly
625             630             635                 640

Ser Lys Glu Phe Gly Phe Arg Gln Gln Val Leu Glu Asp Thr Ile Gln
                645             650             655

Pro Ala Ile Asp Ser Gly Lys Gly Leu Met Phe Thr Gln Pro Asn Gln
                660             665             670

Ala Ala Gly Tyr Met Ala Lys Leu Ile Trp Glu Ser Val Ser Val Thr
            675             680             685

Val Val Ala Ala Val Glu Ala Met Asn Trp Leu Lys Ser Ala Ala Lys
        690             695             700

Leu Leu Ala Ala Glu Val Lys Asp Lys Lys Thr Gly Glu Ile Leu Arg
705             710             715                 720

Lys Arg Cys Ala Val His Trp Val Thr Pro Asp Gly Phe Pro Val Trp
                725             730             735

Gln Glu Tyr Lys Lys Pro Ile Gln Thr Arg Leu Asn Leu Met Phe Leu
                740             745             750

Gly Gln Phe Arg Leu Gln Pro Thr Ile Asn Thr Asn Lys Asp Ser Glu
            755             760             765

Ile Asp Ala His Lys Gln Glu Ser Gly Ile Ala Pro Asn Phe Val His
        770             775             780

Ser Gln Asp Gly Ser His Leu Arg Lys Thr Val Trp Ala His Glu
785             790             795                 800

Lys Tyr Gly Ile Glu Ser Phe Ala Leu Ile His Asp Ser Phe Gly Thr
                805             810             815

Ile Pro Ala Asp Ala Ala Asn Leu Phe Lys Ala Val Arg Glu Thr Met
                820             825             830

Val Asp Thr Tyr Glu Ser Cys Asp Val Leu Ala Asp Phe Tyr Asp Gln
            835             840             845

Phe Ala Asp Gln Leu His Glu Ser Gln Leu Lys Met Pro Ala Leu
        850             855             860

Pro Ala Lys Gly Asn Leu Asn Leu Arg Asp Ile Leu Glu Ser Asp Phe
865             870             875                 880
```

Ala Phe Ala

<210> SEQ ID NO 19
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Leu variant of T7 DNA-dependent RNA polymerase, including start codon encoding N-terminal methionine; corresponding to #10 in Table 3

<400> SEQUENCE: 19

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga cgcatcaag    1440
ttcattgagg aaaaccacga aacatcatg gcttgcgcta gtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
```

```
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 20
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Leu variant of T7 DNA-
      dependent RNA polymerase, amino acid sequence including N-terminal
      methionine; corresponding to #10 in Table 3

<400> SEQUENCE: 20

```
Met Asn Thr Ile Asn Ile Ala Lys Asn Asp Phe Ser Asp Ile Glu Leu
 1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

-continued

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys

| | | | | | | | | | | | | |
|---|---|---|---|---|---|---|---|---|---|---|---|---|
| | | 595 | | | | 600 | | | | 605 | | |
| Val | Lys | Leu | Gly | Thr | Lys | Ala | Leu | Ala | Gly | Gln | Trp | Leu | Ala | Tyr | Gly |
| | | 610 | | | | | 615 | | | | | 620 | | | |

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 21
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Ile variant of
      T7 DNA-dependent RNA polymerase, including start codon encoding
      N-terminal methionine; corresponding to #11 in Table 3

<400> SEQUENCE: 21
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240

```
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggg ccattgagga cgaggctcgc ttcggtcgta tccgtgacct tgaagctaag      480
cacttcaaga aaaacgttga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg gtcgtatcta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gcttgcgcta agtctccact ggagaacact     1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga aaagtcaag ctgggcacta aggcactggc tggtcaatgg     1860
ctggcttacg gtgttactcg cagtgtgact aagcgttcag tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta agctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctgtagtgtg gcacacgag     2400 aagtacggaa tcgaatcttt tgcactgatt cacgactcct tcggtaccat tccggctgac     2460
gctgcgaacc tgttcaaagc agtgcgcgaa actatggttg acacatatga gtcttgtgat     2520
gtactggctg atttctacga ccagttcgct gaccagttgc acgagtctca attggacaaa     2580
atgccagcac ttccggctaa aggtaacttg aacctccgtg acatcttaga gtcggacttc     2640
```

```
gcgttcgcgt aataa                                                    2655
```

<210> SEQ ID NO 22
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Ile variant of T7 DNA-dependent RNA
      polymerase, amino acid sequence including N-terminal methionine;
      corresponding to #11 in Table 3

<400> SEQUENCE: 22

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320
```

-continued

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Ile Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu

```
              740                  745                  750
Gly Gln Phe Arg Leu Gln Pro Thr Ile Asn Thr Asn Lys Asp Ser Glu
            755                  760                  765

Ile Asp Ala His Lys Gln Glu Ser Gly Ile Ala Pro Asn Phe Val His
        770                  775                  780

Ser Gln Asp Gly Ser His Leu Arg Lys Thr Val Val Trp Ala His Glu
785                  790                  795                  800

Lys Tyr Gly Ile Glu Ser Phe Ala Leu Ile His Asp Ser Phe Gly Thr
                805                  810                  815

Ile Pro Ala Asp Ala Ala Asn Leu Phe Lys Ala Val Arg Glu Thr Met
            820                  825                  830

Val Asp Thr Tyr Glu Ser Cys Asp Val Leu Ala Asp Phe Tyr Asp Gln
        835                  840                  845

Phe Ala Asp Gln Leu His Glu Ser Gln Leu Asp Lys Met Pro Ala Leu
    850                  855                  860

Pro Ala Lys Gly Asn Leu Asn Leu Arg Asp Ile Leu Glu Ser Asp Phe
865                  870                  875                  880

Ala Phe Ala

<210> SEQ ID NO 23
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Ile
      variant of T7 DNA-dependent RNA polymerase, including start codon
      encoding N-terminal methionine; corresponding to #12 in Table 3

<400> SEQUENCE: 23
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggtt cgtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
```

```
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtatcta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga cgcatcaag    1440 ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 24
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Ile variant of T7 DNA-
      dependent RNA polymerase, amino acid sequence including N-terminal
      methionine; corresponding to #12 in Table 3

<400> SEQUENCE: 24

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

```
Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65              70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Ile Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460
```

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 25
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Phe variant of
T7 DNA-dependent RNA polymerase, including start codon encoding
N-terminal methionine; corresponding to #13 in Table 3

<400> SEQUENCE: 25

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttgaa ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960
aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg aaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtttcta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga cgcatcaag    1440
ttcattgagg aaaaccacga gaacatcatg gcttgcgcta gtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
```

```
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 26
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Phe variant of T7 DNA-dependent RNA
      polymerase, amino acid sequence including N-terminal methionine;
      corresponding to #13 in Table 3

<400> SEQUENCE: 26

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190
```

```
Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Gly Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Phe Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605
```

```
Val Lys Leu Gly Thr Lys Ala Leu Ala Gly Gln Trp Leu Ala Tyr Gly
    610             615                 620
Val Thr Arg Ser Val Thr Lys Arg Ser Val Met Thr Leu Ala Tyr Gly
625             630                 635                 640
Ser Lys Glu Phe Gly Phe Arg Gln Gln Val Leu Glu Asp Thr Ile Gln
            645                 650                 655
Pro Ala Ile Asp Ser Gly Lys Gly Leu Met Phe Thr Gln Pro Asn Gln
        660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 27
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Phe
      variant of T7 DNA-dependent RNA polymerase, including start codon
      encoding N-terminal methionine; corresponding to #14 in Table 3

<400> SEQUENCE: 27
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
```

-continued

```
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtttcta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga cgcatcaag    1440 ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg tgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta gctgctggc tgctgaggtc aaagataaga agactggaga gattcttcgc   2160
aagcgtagcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg gcacacgag   2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 28
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Phe variant of T7 DNA-
      dependent RNA polymerase, amino acid sequence including N-terminal
      methionine; corresponding to #14 in Table 3

<400> SEQUENCE: 28

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335
```

```
Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Phe Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750
```

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 29
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Ser633Met variant of
      T7 DNA-dependent RNA polymerase, including start codon encoding
      N-terminal methionine; corresponding to #15 in Table 3

<400> SEQUENCE: 29
atgaacacga ttaacatcgc taagaacgac ttctctgaca tcgaactggc tgctatcccg      60
ttcaacactc tggctgacca ttacggtgag cgtttagctc gcaacagtt ggcccttgag      120 catgagtctt acgagatggg tgaagcacgc ttccgcaaga tgtttgagcg tcaacttaaa     180
gctggtgagg ttgcggataa cgctgccgcc aagcctctca tcactaccct actccctaag    240
atgattgcac gcatcaacga ctggtttgag gaagtgaaag ctaagcgcgg caagcgcccg     300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct gaagctaag     480 cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg     780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag cctagcggt cgccaacgta     1020 atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct    1140

```
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgtttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga aacatcatg gcttgcgcta agtctccact ggagaacact    1500
tggtgggctg agcaagattc tccgttctgc ttccttgcgt tctgctttga gtacgctggg    1560
gtacagcacc acgcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgtatgg tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 30
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Ser633Met variant of T7 DNA-dependent RNA
      polymerase, amino acid sequence including N-terminal methionine;
      corresponding to #15 in Table 3

<400> SEQUENCE: 30

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
```

```
                50                  55                  60
Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
                130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480
```

```
Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Met Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

```
<210> SEQ ID NO 31
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Ser633Met
      variant of T7 DNA-dependent RNA polymerase, including start codon
      encoding N-terminal methionine; corresponding to #16 in Table 3

<400> SEQUENCE: 31
```

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | ctgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | gtcgtgttta | cgctgtgtca | atgttcaacc | cgcaaggtaa | cgatatgacc | 1320 |
| aaaggactgc | ttacgctggc | gaaaggtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | gaacatcatg | gcttgcgcta | agtctccact | ggagaacact | 1500 |
| tggtgggctg | agcaagattc | tccgttctgc | ttccttgcgt | tctgctttga | gtacgctggg | 1560 |
| gtacagcacc | acggcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattg | ttgctaagaa | agtcaacgag | 1740 |
| attctacaag | cagacgcaat | caatgggacc | gataacgaag | tagttaccgt | gaccgatgag | 1800 |
| aacactggtg | aaatctctga | aaagtcaag | ctgggcacta | aggcactggc | tggtcaatgg | 1860 |
| ctggcttacg | gtgttactcg | cagtgtgact | aagcgtatgg | tcatgacgct | ggcttacggg | 1920 |

-continued

```
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg gcacacgag     2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 32
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: DNA sequence encoding the Cys723Ser, Ser633Met
      variant of T7 DNA-dependent RNA polymerase, including start codon
      encoding N-terminal methionine; corresponding to #16 in Table 3

<400> SEQUENCE: 32

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
```

```
            195                 200                 205
Ser Ile His Val Gly Val Arg Cys Ile Glu Met Leu Ile Glu Ser Thr
210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
                355                 360                 365
Met Asn Pro Glu Ala Leu Thr Ala Trp Lys Arg Ala Ala Ala Val
370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
            610                 615                 620
```

-continued

```
Val Thr Arg Ser Val Thr Lys Arg Met Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 33
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val650Leu variant of
      T7 DNA-dependent RNA polymerase, including start codon encoding
      N-terminal methionine; corresponding to #17 in Table 3

<400> SEQUENCE: 33
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
```

```
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttgga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaactg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag    2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

```
<210> SEQ ID NO 34
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val650Leu variant of T7 DNA-dependent RNA
      polymerase, amino acid sequence including N-terminal methionine;
      corresponding to #17 in Table 3

<400> SEQUENCE: 34

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
```

```
                    340                 345                 350
Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Leu Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765
```

-continued

```
Ile Asp Ala His Lys Gln Glu Ser Gly Ile Ala Pro Asn Phe Val His
         770                 775                 780

Ser Gln Asp Gly Ser His Leu Arg Lys Thr Val Trp Ala His Glu
785                 790                 795                 800

Lys Tyr Gly Ile Glu Ser Phe Ala Leu Ile His Asp Ser Phe Gly Thr
                 805                 810                 815

Ile Pro Ala Asp Ala Ala Asn Leu Phe Lys Ala Val Arg Glu Thr Met
                 820                 825                 830

Val Asp Thr Tyr Glu Ser Cys Asp Val Leu Ala Asp Phe Tyr Asp Gln
             835                 840                 845

Phe Ala Asp Gln Leu His Glu Ser Gln Leu Asp Lys Met Pro Ala Leu
         850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 35
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val650Leu
      variant of T7 DNA-dependent RNA polymerase, including start codon
      encoding N-terminal methionine; corresponding to #18 in Table 3

<400> SEQUENCE: 35
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
```

```
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaactg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta gctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 36
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val650Leu variant of T7 DNA-
      dependent RNA polymerase, amino acid sequence including N-terminal
      methionine; corresponding to #18 in Table 3

<400> SEQUENCE: 36

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

```
Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
```

```
                485                 490                 495
Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Leu Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 37
<211> LENGTH: 2655
```

<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Thr654Leu variant of
      T7 DNA-dependent RNA polymerase, including start codon encoding
      N-terminal methionine; corresponding to #19 in Table 3

<400> SEQUENCE: 37

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg tgttactcg cagtgtgact aagcgttcag tcatgacgct ggcttacggg    1920
tccaaagagt tcggcttccg tcaacaagtg ctggaagatc tgattcagcc agctattgat    1980
```

-continued

```
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 38
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Thr654Leu variant of T7 DNA-dependent RNA
      polymerase, amino acid sequence including N-terminal methionine;
      corresponding to #19 in Table 3

<400> SEQUENCE: 38

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205
```

```
Ser Ile His Val Gly Val Arg Cys Ile Glu Met Leu Ile Glu Ser Thr
210                 215                 220
Gly Met Val Ser Leu His Arg Gln Asn Ala Gly Val Val Gly Gln Asp
225                 230                 235                 240
Ser Glu Thr Ile Glu Leu Ala Pro Tyr Ala Glu Ala Ile Ala Thr
                245                 250                 255
Arg Ala Gly Ala Leu Ala Gly Ile Ser Pro Met Phe Gln Pro Cys Val
                260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
                340                 345                 350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
            435                 440                 445
Gly Lys Pro Ile Gly Lys Glu Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
```

```
              625                 630                 635                 640
    Ser Lys Glu Phe Gly Phe Arg Gln Gln Val Leu Glu Asp Leu Ile Gln
                    645                 650                 655

Pro Ala Ile Asp Ser Gly Lys Gly Leu Met Phe Thr Gln Pro Asn Gln
                    660                 665                 670

Ala Ala Gly Tyr Met Ala Lys Leu Ile Trp Glu Ser Val Ser Val Thr
                    675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
    705                 710                 715                 720

Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
                    740                 745                 750

Gly Gln Phe Arg Leu Gln Pro Thr Ile Asn Thr Asn Lys Asp Ser Glu
                    755                 760                 765

Ile Asp Ala His Lys Gln Glu Ser Gly Ile Ala Pro Asn Phe Val His
                    770                 775                 780

Ser Gln Asp Gly Ser His Leu Arg Lys Thr Val Val Trp Ala His Glu
    785                 790                 795                 800

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                    820                 825                 830

Val Asp Thr Tyr Glu Ser Cys Asp Val Leu Ala Asp Phe Tyr Asp Gln
                    835                 840                 845

Phe Ala Asp Gln Leu His Glu Ser Gln Leu Asp Lys Met Pro Ala Leu
                    850                 855                 860

Pro Ala Lys Gly Asn Leu Asn Leu Arg Asp Ile Leu Glu Ser Asp Phe
    865                 870                 875                 880

Ala Phe Ala

<210> SEQ ID NO 39
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Thr654Leu
      variant of T7 DNA-dependent RNA polymerase, including start codon
      encoding N-terminal methionine; corresponding to #20 in Table 3

<400> SEQUENCE: 39
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
```

```
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg tgttactcg cagtgtgact aagcgttcag tcatgacgct ggcttacggg   1920
tccaaagagt tcggcttccg tcaacaagtg ctggaagatc tgattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgtagcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                   2655
```

<210> SEQ ID NO 40
<211> LENGTH: 883

```
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Thr654Leu variant of T7 DNA-
      dependent RNA polymerase, amino acid sequence including
      N-terminal methionine; corresponding to #20 in Table 3

<400> SEQUENCE: 40

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350
```

-continued

```
Pro Ala Ile Glu Arg Glu Glu Leu Pro Met Lys Pro Glu Asp Ile Asp
            355                 360                 365
Met Asn Pro Glu Ala Leu Thr Ala Trp Lys Arg Ala Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Leu Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Ala Ala Lys
            690                 695                 700
Leu Leu Ala Ala Glu Val Lys Asp Lys Thr Gly Glu Ile Leu Arg
705                 710                 715                 720
Lys Arg Ser Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
```

|  | 770 |  | 775 |  | 780 |  |  |  |  |
|--|--|--|--|--|--|--|--|--|--|

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 41
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Ala702Val variant of
    T7 DNA-dependent RNA polymerase, including start codon encoding
    N-terminal methionine; corresponding to #21 in Table 3

<400> SEQUENCE: 41
atgaacacga ttaacatcgc taagaacgac ttctctgaca tcgaactggc tgctatcccg     60
ttcaacactc tggctgacca ttacggtgag cgtttagctc gcaacagtt ggcccttgag    120 catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260

```
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgttgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 42
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Ala702Val variant of T7 DNA-dependent RNA
      polymerase, amino acid sequence including N-terminal methionine;
      corresponding to #21 in Table 3

<400> SEQUENCE: 42

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80
```

```
Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Ala Val
            370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

| | | | | | | | | | | | | |
|---|---|---|---|---|---|---|---|---|---|---|---|---|
|Leu|Glu|Asn|Thr 500|Trp|Trp|Ala|Glu|Gln 505|Asp|Ser|Pro|Phe Cys Phe Leu 510|
|Ala|Phe|Cys 515|Phe|Glu|Tyr|Ala 520|Gly|Val|Gln|His|His 525|Gly Leu Ser Tyr|
|Asn|Cys 530|Ser|Leu|Pro|Leu 535|Ala|Phe|Asp|Gly|Ser 540|Cys|Ser Gly Ile Gln|
|His 545|Phe|Ser|Ala|Met 550|Leu|Arg|Asp|Glu|Val 555|Gly|Gly|Arg Ala Val Asn 560|

Leu Glu Asn Thr Trp Trp Ala Glu Gln Asp Ser Pro Phe Cys Phe Leu
                500                     505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
        580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
        610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Val Ala Lys
        690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
        850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 43
<211> LENGTH: 2655
<212> TYPE: DNA
<213> ORGANISM: Artificial Sequence -continued
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Ala702Val
      variant of T7 DNA-dependent RNA polymerase, including start codon
      encoding N-terminal methionine; corresponding to #22 in Table 3

<400> SEQUENCE: 43

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgaccte | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | gctaacggt | cgtcgtcctc | tggcgctggt | gcgtactcac | 900 |
| agtaagaaag | cactgatgcg | ctacgaagac | gtttacatgc | ctgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | gtcgtgttta | cgctgtgtca | atgttcaacc | cgcaaggtaa | cgatatgacc | 1320 |
| aaaggactgc | ttacgctggc | gaaaggtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | gaacatcatg | gcttgcgcta | agtctccact | ggagaacact | 1500 |
| tggtgggctc | agcaagattc | tccgttctgc | ttccttgcgt | tctgctttga | gtacgctggg | 1560 |
| gtacagcacc | acggcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattg | ttgctaagaa | agtcaacgag | 1740 |
| attctacaag | cagacgcaat | caatgggacc | gataacgaag | tagttaccgt | gaccgatgag | 1800 |
| aacactggtg | aaatctctga | aaagtcaag | ctgggcacta | aggcactggc | tggtcaatgg | 1860 |
| ctggcttacg | gtgttactcg | cagtgtgact | aagcgttcag | tcatgacgct | ggcttacggg | 1920 |
| tccaaagagt | tcggcttccg | tcaacaagtg | ctggaagata | ccattcagcc | agctattgat | 1980 |
| tccggcaagg | gtctgatgtt | cactcagccg | aatcaggctg | ctggatacat | ggctaagctg | 2040 |

```
atttgggaat ctgtgagcgt gacggtggta gctgcggttg aagcaatgaa ctggcttaag     2100
tctgttgcta agctgctggc tgctgaggtc aaagataaga agactggaga gattcttcgc     2160
aagcgtagcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctgtagtgtg ggcacacgag     2400
aagtacggaa tcgaatcttt tgcactgatt cacgactcct tcggtaccat tccggctgac     2460
gctgcgaacc tgttcaaagc agtgcgcgaa actatggttg acacatatga gtcttgtgat     2520
gtactggctg atttctacga ccagttcgct gaccagttgc acgagtctca attggacaaa     2580
atgccagcac ttccggctaa aggtaacttg aacctccgtg acatcttaga gtcggacttc     2640
gcgttcgcgt aataa                                                      2655
```

<210> SEQ ID NO 44
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Ala702Val variant of T7 DNA-
    dependent RNA polymerase, amino acid sequence including N-terminal
    methionine; corresponding to #22 in Table 3

<400> SEQUENCE: 44

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

```
Gly Met Val Ser Leu His Arg Gln Asn Ala Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Val Ala Lys
    690                 695                 700
Leu Leu Ala Ala Glu Val Lys Asp Lys Lys Thr Gly Glu Ile Leu Arg
705                 710                 715                 720
Lys Arg Ser Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala
```

<210> SEQ ID NO 45
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val795Ile variant of
    T7 DNA-dependent RNA polymerase, including start codon encoding
    N-terminal methionine; corresponding to #23 in Table 3

<400> SEQUENCE: 45

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
```

-continued

```
cacttcaaga aaaacgttga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg gctaacggt cgtcgtcctc tggcgctggt gcgtactcac       900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtgtttta cgctgtgtca atgttcaacc cgcaaggtaa cgatatgacc     1320
aaaggactgc ttacgctggc gaaagtaaa ccaatcggta aggaaggtta ctactggctg      1380
aaaatccacg gtgcaaactg tgcgggtgtc gataaggttc cgttccctga gcgcatcaag     1440
ttcattgagg aaaaccacga gaacatcatg gcttgcgcta gtctccact ggagaacact      1500 tggtgggctg agcaagattc tccgttctgc ttccttgcgt tctgctttga gtacgctggg     1560
gtacagcacc acgcctgag ctataactgc tcccttccgc tggcgtttga cgggtcttgc      1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct     2340
aactttgtac acagccaaga cggtagccac cttcgtaaga ctatcgtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 46
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val795Ile variant of T7 DNA-dependent RNA
      polymerase, amino acid sequence including N-terminal methionine;
      corresponding to #23 in Table 3

<400> SEQUENCE: 46

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365
```

```
Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
    770                 775                 780
```

-continued

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 47
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val795Ile
      variant of T7 DNA-dependent RNA polymerase, including start codon
      encoding N-terminal methionine; corresponding to #24 in Table 3

<400> SEQUENCE: 47

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataggcca tctggttccc ttacaacatg    1260
gactggcgcg gtcgtgttta cgctgtgtca atgttcaacc cgcaaggtaa cgatatgacc    1320
```

-continued

```
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                      2655
```

<210> SEQ ID NO 48
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val795Ile variant of T7
    DNA-dependent RNA polymerase, amino acid sequence including
    N-terminal methionine; corresponding to #24 in Table 3

<400> SEQUENCE: 48

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
```

-continued

```
                85                  90                  95
Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 49
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Ala702Val, Val795Ile
      variant of T7 DNA-dependent RNA polymerase, including start codon
      encoding N-terminal methionine; corresponding to #25 in Table 3

<400> SEQUENCE: 49

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | tctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | tgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | gtcgtgttta | cgctgtgtca | atgttcaacc | cgcaaggtaa | cgatatgacc | 1320 |
| aaaggactgc | ttacgctggc | gaaaggtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | aacatcatg | gcttgcgcta | gtctccact | ggagaacact | 1500 |
| tggtgggctg | agcaagattc | tccgttctgc | ttccttgcgt | tctgctttga | gtacgctggg | 1560 |
| gtacagcacc | acggcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattg | ttgctaagaa | agtcaacgag | 1740 |
| attctacaag | cagacgcaat | caatgggacc | gataacgaag | tagttaccgt | gaccgatgag | 1800 |
| aacactggtg | aaatctctga | aaagtcaag | ctgggcacta | aggcactggc | tggtcaatgg | 1860 |
| ctggcttacg | gtgttactcg | cagtgtgact | aagcgttcag | tcatgacgct | ggcttacggg | 1920 |
| tccaaagagt | tcggcttccg | tcaacaagtg | ctggaagata | ccattcagcc | agctattgat | 1980 |
| tccggcaagg | gtctgatgtt | cactcagccg | aatcaggctg | ctggatacat | ggctaagctg | 2040 |
| atttgggaat | ctgtgagcgt | gacggtggta | gctgcggttg | aagcaatgaa | ctggcttaag | 2100 |

```
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctatcgtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 50
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Ala702Val, Val795Ile variant of T7
      DNA-dependent RNA polymerase, amino acid sequence including
      N-terminal methionine; corresponding to #25 in Table 3

<400> SEQUENCE: 50

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
```

-continued

```
                225                 230                 235                 240
        Ser Glu Thr Ile Glu Leu Ala Pro Gly Tyr Ala Glu Ala Ile Ala Thr
                        245                 250                 255

Arg Ala Gly Ala Leu Ala Gly Ile Ser Pro Met Phe Gln Pro Cys Val
                        260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
        305                 310                 315                 320

Asn Ile Ala Gln Asn Thr Ala Trp Lys Ile Asn Lys Lys Val Leu Ala
                        325                 330                 335

Val Ala Asn Val Ile Thr Lys Trp Lys His Cys Pro Val Glu Asp Ile
                        340                 345                 350

Pro Ala Ile Glu Arg Glu Glu Leu Pro Met Lys Pro Glu Asp Ile Asp
                        355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Arg Ile Ser Leu Glu Phe
        385                 390                 395                 400

Met Leu Glu Gln Ala Asn Lys Phe Ala Asn His Lys Ala Ile Trp Phe
                        405                 410                 415

Pro Tyr Asn Met Asp Trp Arg Gly Arg Val Tyr Ala Val Ser Met Phe
                        420                 425                 430

Asn Pro Gln Gly Asn Asp Met Thr Lys Gly Leu Leu Thr Leu Ala Lys
                        435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
        465                 470                 475                 480

Phe Ile Glu Glu Asn His Glu Asn Ile Met Ala Cys Ala Lys Ser Pro
                        485                 490                 495

Leu Glu Asn Thr Trp Trp Ala Glu Gln Asp Ser Pro Phe Cys Phe Leu
                        500                 505                 510

Ala Phe Cys Phe Glu Tyr Ala Gly Val Gln His His Gly Leu Ser Tyr
                        515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
        545                 550                 555                 560

Leu Leu Pro Ser Glu Thr Val Gln Asp Ile Tyr Gly Ile Val Ala Lys
                        565                 570                 575

Lys Val Asn Glu Ile Leu Gln Ala Asp Ala Ile Asn Gly Thr Asp Asn
                        580                 585                 590

Glu Val Val Thr Val Thr Asp Glu Asn Thr Gly Glu Ile Ser Glu Lys
                        595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
        625                 630                 635                 640

Ser Lys Glu Phe Gly Phe Arg Gln Gln Val Leu Glu Asp Thr Ile Gln
                        645                 650                 655
```

```
Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Val Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 51
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Ala702Val,
      Val795Ile variant of T7 DNA-dependent RNA polymerase, including
      start codon encoding N-terminal methionine; corresponding to #26
      in Table 3

<400> SEQUENCE: 51
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaaacgttga ggaacaactc aacaagcgcg tagggcacgt ctacaagaaa     540
```

-continued

```
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaagtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctc tggatacat ggctaagctg    2040 atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgtagcg ctgtgcattg ggtaactcct gatggttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                      2655
```

<210> SEQ ID NO 52
<211> LENGTH: 883
<212> TYPE: PRT
<213> ORGANISM: Artificial Sequence
<220> FEATURE:

<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Ala702Val, Val795Ile variant of T7
    DNA-dependent RNA polymerase, amino acid sequence including
    N-terminal methionine; corresponding to #26 in Table 3

<400> SEQUENCE: 52

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365
```

-continued

```
Met Asn Pro Glu Ala Leu Thr Ala Trp Lys Arg Ala Ala Ala Val
    370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                    405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                435                 440                 445
Gly Lys Pro Ile Gly Lys Glu Gly Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
                610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
                675                 680                 685
Val Val Ala Ala Val Glu Ala Met Asn Trp Leu Lys Ser Val Ala Lys
                690                 695                 700
Leu Leu Ala Ala Glu Val Lys Asp Lys Lys Thr Gly Glu Ile Leu Arg
705                 710                 715                 720
Lys Arg Ser Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
                755                 760                 765
Ile Asp Ala His Lys Gln Glu Ser Gly Ile Ala Pro Asn Phe Val His
770                 775                 780
Ser Gln Asp Gly Ser His Leu Arg Lys Thr Ile Val Trp Ala His Glu
```

```
                785                 790                 795                 800
Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 53
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Leu, Ala702Val
      variant of T7 DNA-dependent RNA polymerase, including start codon
      encoding N-terminal methionine; corresponding to #27 in Table 3

<400> SEQUENCE: 53
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct tgaagctaag     480
cacttcaaga aaaacgttga ggaacaactc aacaagcgcg tagggcacgt ctacaagaaa     540
gcatttatgc aagttgtcga ggctgacatg ctctctaagg tctactcgg tggcgaggcg     600 tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
```

```
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga acatcatg gcttgcgcta agtctccact ggagaacact     1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtgta gctgcgcgttg aagcaatgaa ctggcttaag    2100
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 54
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Leu, Ala702Val variant of T7
      DNA-dependent RNA polymerase, amino acid sequence including
      N-terminal methionine; corresponding to #27 in Table 3

<400> SEQUENCE: 54

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95
```

```
Gly Lys Arg Pro Thr Ala Phe Gln Phe Leu Gln Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Glu Ala Asp Met Leu Ser
            180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Val Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 55
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:

<221> NAME/KEY: misc_feature
<222> LOCATION: (1)..(2655)
<223> OTHER INFORMATION: DNA sequence encoding the Cys723Ser, Val426Leu, Ala702Val variant of T7 DNA-dependent RNA polymerase, including start codon encoding N-terminal methionine; corresponding to #28 in Table 3

<400> SEQUENCE: 55

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgaccct tgaagctaag     480 cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtctgta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga aacatcatg gcttgcgcta gtctccact ggagaacact    1500 tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattt tgctaagaa agtcaacgag    1740 attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
```

```
tctgttgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct     2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 56
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Leu, Ala702Val variant of T7
      DNA-dependent RNA polymerase, amino acid sequence including
      N-terminal methionine; corresponding to #28 in Table 3

<400> SEQUENCE: 56

```
Met Asn Thr Ile Asn Ile Ala Lys Asn Asp Phe Ser Asp Ile Glu Leu
 1               5                  10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
           100                 105                 110

Ala Val Ala Tyr Ile Thr Ile Lys Thr Thr Leu Ala Cys Leu Thr Ser
       115                 120                 125

Ala Asp Asn Thr Thr Val Gln Ala Val Ala Ser Ala Ile Gly Arg Ala
   130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
           180                 185                 190

Lys Gly Leu Leu Gly Gly Glu Ala Trp Ser Ser Trp His Lys Glu Asp
       195                 200                 205

Ser Ile His Val Gly Val Arg Cys Ile Glu Met Leu Ile Glu Ser Thr
   210                 215                 220

Gly Met Val Ser Leu His Arg Gln Asn Ala Gly Val Val Gly Gln Asp
```

```
            225                 230                 235                 240
Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655
```

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 57
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Leu, Val795Ile
      variant of T7 DNA-dependent RNA polymerase, including start codon
      encoding N-terminal methionine; corresponding to #29 in Table 3

<400> SEQUENCE: 57
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaaacgttga ggaacaactc aacaagcgcg tagggcacgt ctacaagaaa     540

```
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag acatccctg cgattgagcg tgaagaactc      1080
ccgatgaaac cggaagacat cgacatgaat cctgaggctc tcaccgcgtg aaacgtgct      1140 gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg gtcgtctgta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gcttgcgcta agtctccact ggagaacact     1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga gaaagtcaag ctgggcacta aggcactggc tggtcaatgg     1860
ctggcttacg gtgttactcg cagtgtgact aagcgttcag tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta gctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctatcgtgtg ggcacacgag     2400
aagtacggaa tcgaatcttt tgcactgatt cacgactcct tcggtaccat tccggctgac     2460
gctgcgaacc tgttcaaagc agtgcgcgaa actatggttg acacatatga gtcttgtgat     2520
gtactggctg atttctacga ccagttcgct gaccagttgc acgagtctca attggacaaa     2580
atgccagcac ttccggctaa aggtaacttg aacctccgtg acatcttaga gtcggacttc     2640
gcgttcgcgt aataa                                                     2655
```

<210> SEQ ID NO 58
<211> LENGTH: 883
<212> TYPE: PRT
<213> ORGANISM: Artificial Sequence
<220> FEATURE:
<223> OTHER INFORMATION: Synthetic variant polypeptide

```
<220> FEATURE:
<221> NAME/KEY: MISC_FEATURE
<222> LOCATION: (1)..(883)
<223> OTHER INFORMATION: Val426Leu, Val795Ile variant of T7
      DNA-dependent RNA polymerase, amino acid sequence including
      N-terminal methionine; corresponding to #29 in Table 3

<400> SEQUENCE: 58

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
```

-continued

```
            370                 375                 380
Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                    405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                    485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                    565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                    645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                    725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Ile Val Trp Ala His Glu
785                 790                 795                 800
```

```
Lys Tyr Gly Ile Glu Ser Phe Ala Leu Ile His Asp Ser Phe Gly Thr
            805                 810                 815
Ile Pro Ala Asp Ala Ala Asn Leu Phe Lys Ala Val Arg Glu Thr Met
        820                 825                 830
Val Asp Thr Tyr Glu Ser Cys Asp Val Leu Ala Asp Phe Tyr Asp Gln
    835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 59
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Leu,
      Val795Ile variant of T7 DNA-dependent RNA polymerase, including
      start codon encoding N-terminal methionine; corresponding to #30
      in Table 3

<400> SEQUENCE: 59
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggc ccattgagga cgaggctcgc ttcggtcgta ccgtgaccct gaagctaag      480 cacttcaaga aaacgttga ggaacaactc aacaagcgcg tagggcacgt ctacaagaaa     540
gcatttatgc aagttgtcga ggctgacatg ctctctaagg tctactcgg tggcgaggcg     600 tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
```

```
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga aacatcatg gcttgcgcta agtctccact ggagaacact    1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg    1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcgcgttg aagcaatgaa ctggcttaag   2100
tctgctgcta agctgctggc tgctgaggtc aaagataaga agactggaga gattcttcgc   2160
aagcgtagcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctatcgtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                   2655
```

<210> SEQ ID NO 60
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: DNA sequence encoding the Cys723Ser, Val426Leu,
      Val795Ile variant of T7 DNA-dependent RNA polymerase, including
      start codon encoding N-terminal methionine; corresponding to #30
      in Table 3

<400> SEQUENCE: 60

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
```

```
                         85                  90                  95
Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 61
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Leu, Ala702Val,
      Val795Ile variant of T7 DNA-dependent RNA polymerase, including
      start codon encoding N-terminal methionine; corresponding to #31
      in Table 3

<400> SEQUENCE: 61

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggc ccattgagga cgaggctcgc ttcggtcgta ccgtgaccct gaagctaag      480 cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag acatccctg cgattgagcg tgaagaactc     1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtctgta cgctgtgtca atgttcaacc gcaaggtaa cgatatgacc    1320 aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga aacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctc tggatacat ggctaagctg    2040 atttgggaat ctgtgagcgt gacggtggta gctgcggttg aagcaatgaa ctggcttaag    2100
```

-continued

```
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 62
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Leu, Ala702Val, Val795Ile variant of T7
      DNA-dependent RNA polymerase, amino acid sequence including
      N-terminal methionine; corresponding to #31 in Table 3

<400> SEQUENCE: 62

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
```

```
                    645                 650                 655
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 63
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Leu,
      Ala702Val, Val795Ile variant of T7 DNA-dependent RNA polymerase,
      including start codon encoding N-terminal methionine;
      corresponding to #32 in Table 3

<400> SEQUENCE: 63
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
```

| | |
|---|---|
| cacttcaaga aaaacgttga ggaacaactc aacaagcgcg tagggcacgt ctacaagaaa | 540 |
| gcatttatgc aagttgtcga ggctgacatg ctctctaagg gtctactcgg tggcgaggcg | 600 |
| tggtcttcgt ggcataagga agactctatt catgtaggag tacgctgcat cgagatgctc | 660 |
| attgagtcaa ccggaatggt tagcttacac cgccaaaatg ctggcgtagt aggtcaagac | 720 |
| tctgagacta tcgaactcgc acctgaatac gctgaggcta tcgcaacccg tgcaggtgcg | 780 |
| ctggctggca tctctccgat gttccaacct tgcgtagttc ctcctaagcc gtggactggc | 840 |
| attactggtg gtggctattg gctaacggt cgtcgtcctc tggcgctggt gcgtactcac | 900 |
| agtaagaaag cactgatgcg ctacgaagac gtttacatgc ctgaggtgta caaagcgatt | 960 |
| aacattgcgc aaaacaccgc atggaaaatc aacaagaaag tcctagcggt cgccaacgta | 1020 |
| atcaccaagt ggaagcattg tccggtcgag acatccctg cgattgagcg tgaagaactc | 1080 |
| ccgatgaaac cggaagacat cgacatgaat cctgaggctc tcaccgcgtg gaaacgtgct | 1140 |
| gccgctgctg tgtaccgcaa ggacaaggct cgcaagtctc gccgtatcag ccttgagttc | 1200 |
| atgcttgagc aagccaataa gtttgctaac cataaggcca tctggttccc ttacaacatg | 1260 |
| gactggcgcg tcgtctgta cgctgtgtca atgttcaacc cgcaaggtaa cgatatgacc | 1320 |
| aaaggactgc ttacgctggc gaaaggtaaa ccaatcggta aggaaggtta ctactggctg | 1380 |
| aaaatccacg gtgcaaactg tgcgggtgtc gataaggttc cgttccctga gcgcatcaag | 1440 |
| ttcattgagg aaaaccacga gaacatcatg gcttgcgcta gtctccact ggagaacact | 1500 |
| tggtgggctg agcaagattc tccgttctgc ttccttgcgt tctgctttga gtacgctggg | 1560 |
| gtacagcacc acggcctgag ctataactgc tcccttccgc tggcgtttga cgggtcttgc | 1620 |
| tctggcatcc agcacttctc cgcgatgctc cgagatgagg taggtggtcg cgcggttaac | 1680 |
| ttgcttccta gtgaaaccgt tcaggacatc tacgggattg ttgctaagaa agtcaacgag | 1740 |
| attctacaag cagacgcaat caatgggacc gataacgaag tagttaccgt gaccgatgag | 1800 |
| aacactggtg aaatctctga gaaagtcaag ctgggcacta aggcactggc tggtcaatgg | 1860 |
| ctggcttacg gtgttactcg cagtgtgact aagcgttcag tcatgacgct ggcttacggg | 1920 |
| tccaaagagt tcggcttccg tcaacaagtg ctggaagata ccattcagcc agctattgat | 1980 |
| tccggcaagg gtctgatgtt cactcagccg aatcaggctg ctggatacat ggctaagctg | 2040 |
| atttgggaat ctgtgagcgt gacggtggta gctgcggttg aagcaatgaa ctggcttaag | 2100 |
| tctgttgcta agctgctggc tgctgaggtc aaagataaga agactggaga gattcttcgc | 2160 |
| aagcgtagcg ctgtgcattg ggtaactcct gatggtttcc ctgtgtggca ggaatacaag | 2220 |
| aagcctattc agacgcgctt gaacctgatg ttcctcggtc agttccgctt acagcctacc | 2280 |
| attaacacca caaagatag cgagattgat gcacacaaac aggagtctgg tatcgctcct | 2340 |
| aactttgtac acagccaaga cggtagccac cttcgtaaga ctatcgtgtg ggcacacgag | 2400 |
| aagtacggaa tcgaatcttt tgcactgatt cacgactcct tcggtaccat tccggctgac | 2460 |
| gctgcgaacc tgttcaaagc agtgcgcgaa actatggttg acacatatga gtcttgtgat | 2520 |
| gtactggctg atttctacga ccagttcgct gaccagttgc acgagtctca attggacaaa | 2580 |
| atgccagcac ttccggctaa aggtaacttg aacctccgtg acatcttaga gtcggacttc | 2640 |
| gcgttcgcgt aataa | 2655 |

<210> SEQ ID NO 64
<211> LENGTH: 883
<212> TYPE: PRT
<213> ORGANISM: Artificial Sequence

```
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Leu, Ala702Val, Val795Ile
      variant of T7 DNA-dependent RNA polymerase, amino acid sequence
      including N-terminal methionine; corresponding to #32 in Table 3

<400> SEQUENCE: 64

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365
```

-continued

```
Met Asn Pro Glu Ala Leu Thr Ala Trp Lys Arg Ala Ala Ala Val
    370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                    405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                    485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Val Ala Lys
    690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
770                 775                 780
```

| | | | | | | | | | | | | | | |
|---|---|---|---|---|---|---|---|---|---|---|---|---|---|---|
|Ser|Gln|Asp|Gly|Ser|His|Leu|Arg|Lys|Thr|Ile|Val|Trp|Ala|His|Glu|
|785| | | |790| | | |795| | | |  | |800|

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 65
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys125Ser, Cys347Ser,
    Cys492Ser, Cys515Ser, Cys723Ser, Cys839Ser, Val426Leu, Ala702Val,
    Val795Ile variant of T7 DNA-dependent RNA polymerase, including
    start codon encoding N-terminal methionine; corresponding to #33
    in Table 3

<400> SEQUENCE: 65

```
atgaacacga ttaacatcgc taagaacgac ttctctgaca tcgaactggc tgctatcccg     60
ttcaacactc tggctgacca ttacggtgag cgtttagctc gcaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg ctagcctaac cagtgctgac aatacaaccg ttcaggctgt agcaagcgca    420
atcggtcggg ccattgagga cgaggctcgc ttcggtcgta ccgtgaccct gaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc tgaggtgta caaagcgatt    960
aacattgcgc aaaacaccgc atggaaaatc aacaagaaag tcctagcggt cgccaacgta   1020
atcaccaagt ggaagcatag cccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
```

```
gactggcgcg gtcgtctgta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gctagcgcta agtctccact ggagaacact    1500
tggtgggctg agcaagattc tccgttctgc ttccttgcgt tcagctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtctagcgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa    2655
```

<210> SEQ ID NO 66
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys125Ser, Cys347Ser, Cys492Ser, Cys515Ser, Cys723Ser, Cys839Ser, Val426Leu, Ala702Val, Val795Ile variant of T7 DNA-dependent RNA polymerase, amino acid sequence including N-terminal methionine; corresponding to #33 in Table 3

<400> SEQUENCE: 66

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
```

```
              65                  70                  75                  80
Met Ile Ala Arg Ile Asn Asp Trp Phe Glu Glu Val Lys Ala Lys Arg
                     85                  90                  95
Gly Lys Arg Pro Thr Ala Phe Gln Phe Leu Gln Glu Ile Lys Pro Glu
            100                 105                 110
Ala Val Ala Tyr Ile Thr Ile Lys Thr Thr Leu Ala Ser Leu Thr Ser
            115                 120                 125
Ala Asp Asn Thr Thr Val Gln Ala Val Ala Ser Ala Ile Gly Arg Ala
            130                 135                 140
Ile Glu Asp Glu Ala Arg Phe Gly Arg Ile Arg Asp Leu Glu Ala Lys
145                 150                 155                 160
His Phe Lys Lys Asn Val Glu Gln Leu Asn Lys Arg Val Gly His
                    165                 170                 175
Val Tyr Lys Lys Ala Phe Met Gln Val Glu Ala Asp Met Leu Ser
                    180                 185                 190
Lys Gly Leu Leu Gly Gly Glu Ala Trp Ser Ser Trp His Lys Glu Asp
            195                 200                 205
Ser Ile His Val Gly Val Arg Cys Ile Glu Met Leu Ile Glu Ser Thr
            210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                    245                 250                 255
Arg Ala Gly Ala Leu Ala Gly Ile Ser Pro Met Phe Gln Pro Cys Val
                    260                 265                 270
Val Pro Pro Lys Pro Trp Thr Gly Ile Thr Gly Gly Tyr Trp Ala
                    275                 280                 285
Asn Gly Arg Arg Pro Leu Ala Leu Val Arg Thr His Ser Lys Lys Ala
            290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                    325                 330                 335
Val Ala Asn Val Ile Thr Lys Trp Lys His Ser Pro Val Glu Asp Ile
                    340                 345                 350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
            370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                    405                 410                 415
Pro Tyr Asn Met Asp Trp Arg Gly Arg Leu Tyr Ala Val Ser Met Phe
                    420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Ser Ala Lys Ser Pro
                    485                 490                 495
```

Leu Glu Asn Thr Trp Trp Ala Glu Gln Asp Ser Pro Phe Cys Phe Leu
            500                 505                 510

Ala Phe Ser Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
    690                 695                 700

Leu Leu Ala Ala Glu Val Lys Asp Lys Lys Thr Gly Glu Ile Leu Arg
705                 710                 715                 720

Lys Arg Ser Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Ser Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 67
<211> LENGTH: 2655
<212> TYPE: DNA

<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Val426Leu, Val650Leu, Ala702Val, Val795Ile variant of T7 DNA-dependent RNA polymerase, including start codon encoding N-terminal methionine; corresponding to #34 in Table 3

<400> SEQUENCE: 67

```
atgaacacga ttaacatcgc taagaacgac ttctctgaca tcgaactggc tgctatcccg      60
ttcaacactc tggctgacca ttacggtgag cgtttagctc gcaacagtt ggcccttgag      120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct tgaagctaag    480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc tgaggtgta caaagcgatt    960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg aaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acgcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaagtcaag ctgggcacta aggcactggc tggtcaatgg    1860
ctggcttacg tgttactcg cagtgtgact aagcgttcag tcatgacgct ggcttacggg    1920
tccaaagagt tcggcttccg tcaacaactg ctggaagata ccattcagcc agctattgat   1980
```

-continued

```
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctatcgtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 68
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Val426Leu, Val650Leu, Ala702Val, Val795Ile
      variant of T7 DNA-dependent RNA polymerase, amino acid sequence
      including N-terminal methionine; corresponding to #34 in Table 3

<400> SEQUENCE: 68

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205
```

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Tyr Ala Glu Ala Ile Ala Thr
            245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly

```
                625           630           635           640
  Ser Lys Glu Phe Gly Phe Arg Gln Gln Leu Leu Glu Asp Thr Ile Gln
                    645               650               655

Pro Ala Ile Asp Ser Gly Lys Gly Leu Met Phe Thr Gln Pro Asn Gln
                660               665               670

Ala Ala Gly Tyr Met Ala Lys Leu Ile Trp Glu Ser Val Ser Val Thr
                    675               680               685

Val Val Ala Ala Val Glu Ala Met Asn Trp Leu Lys Ser Val Ala Lys
                690               695               700

Leu Leu Ala Ala Glu Val Lys Asp Lys Lys Thr Gly Glu Ile Leu Arg
  705               710               715               720

Lys Arg Cys Ala Val His Trp Val Thr Pro Asp Gly Phe Pro Val Trp
                    725               730               735

Gln Glu Tyr Lys Lys Pro Ile Gln Thr Arg Leu Asn Leu Met Phe Leu
                740               745               750

Gly Gln Phe Arg Leu Gln Pro Thr Ile Asn Thr Asn Lys Asp Ser Glu
                    755               760               765

Ile Asp Ala His Lys Gln Glu Ser Gly Ile Ala Pro Asn Phe Val His
                770               775               780

Ser Gln Asp Gly Ser His Leu Arg Lys Thr Ile Val Trp Ala His Glu
  785               790               795               800

Lys Tyr Gly Ile Glu Ser Phe Ala Leu Ile His Asp Ser Phe Gly Thr
                    805               810               815

Ile Pro Ala Asp Ala Ala Asn Leu Phe Lys Ala Val Arg Glu Thr Met
                820               825               830

Val Asp Thr Tyr Glu Ser Cys Asp Val Leu Ala Asp Phe Tyr Asp Gln
                    835               840               845

Phe Ala Asp Gln Leu His Glu Ser Gln Leu Asp Lys Met Pro Ala Leu
                850               855               860

Pro Ala Lys Gly Asn Leu Asn Leu Arg Asp Ile Leu Glu Ser Asp Phe
  865               870               875               880

Ala Phe Ala

<210> SEQ ID NO 69
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the Cys723Ser, Val426Leu,
      Val650Leu, Ala702Val, Val795Ile variant of T7 DNA-dependent RNA
      polymerase, including start codon encoding N-terminal methionine;
      corresponding to #35 in Table 3

<400> SEQUENCE: 69
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
```

```
atcggtcggg ccattgagga cgaggctcgc ttcggtcgta tccgtgacct tgaagctaag     480
cacttcaaga aaaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta gtctccact ggagaacact    1500 tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaactg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 70

```
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: Cys723Ser, Val426Leu, Val650Leu, Ala702Val,
      Val795Ile variant of T7 DNA-dependent RNA polymerase, amino acid
      sequence including N-terminal methionine; corresponding to #35 in
      Table 3

<400> SEQUENCE: 70
```

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile

```
             340                 345                 350
Pro Ala Ile Glu Arg Glu Leu Pro Met Lys Pro Glu Asp Ile Asp
            355                 360                 365
Met Asn Pro Glu Ala Leu Thr Ala Trp Lys Arg Ala Ala Ala Val
        370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Leu Tyr Ala Val Ser Met Phe
                420                 425                 430
Asn Pro Gln Gly Asn Asp Met Thr Lys Gly Leu Leu Thr Leu Ala Lys
            435                 440                 445
Gly Lys Pro Ile Gly Lys Glu Gly Tyr Tyr Trp Leu Lys Ile His Gly
            450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
            515                 520                 525
Asn Cys Ser Leu Pro Leu Ala Phe Asp Gly Ser Cys Ser Gly Ile Gln
            530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
            595                 600                 605
Val Lys Leu Gly Thr Lys Ala Leu Ala Gly Gln Trp Leu Ala Tyr Gly
            610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Leu Leu Glu Asp Thr Ile Gln
                645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Val Ala Lys
            690                 695                 700
Leu Leu Ala Ala Glu Val Lys Asp Lys Lys Thr Gly Glu Ile Leu Arg
705                 710                 715                 720
Lys Arg Ser Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
            755                 760                 765
```

```
Ile Asp Ala His Lys Gln Glu Ser Gly Ile Ala Pro Asn Phe Val His
        770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 71
<211> LENGTH: 2655
<212> TYPE: DNA
<213> ORGANISM: Artificial Sequence
<220> FEATURE:
<223> OTHER INFORMATION: Synthetic coding polynucleotide
<220> FEATURE:
<221> NAME/KEY: misc_feature
<222> LOCATION: (1)..(2655)
<223> OTHER INFORMATION: DNA sequence encoding the C125S, C347S, C492S,
      C515S, C723S, C839S, V426L, V650L, A702V, V795I variant of T7 DNA-
      dependent RNA polymerase, including start codon encoding
      N-terminal methionine; corresponding to #36 in Table 3

<400> SEQUENCE: 71

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg ctagcctaac cagtgctgac aatacaaccg ttcaggctgt agcaagcgca     420
atcggtcggg ccattgagga cgaggctcgc ttcggtcgta ccgtgacct tgaagctaag     480 cacttcaaga aaaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcatag cccggtcgag gacatccctg cgattgagcg tgaagaactc    1080
ccgatgaaac cggaagacat cgacatgaat cctgaggctc tcaccgcgtg gaaacgtgct    1140
```

-continued

```
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gctagcgcta agtctccact ggagaacact    1500
tggtgggctg agcaagattc tccgttctgc ttccttgcgt tcagctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaactg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta gctgctggc tgctgaggtc aaagataaga agactggaga gattcttcgc    2160
aagcgtagcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtctagcgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa    2655
```

<210> SEQ ID NO 72
<211> LENGTH: 883
<212> TYPE: PRT
<213> ORGANISM: Artificial Sequence
<220> FEATURE:
<223> OTHER INFORMATION: Synthetic variant polypeptide
<220> FEATURE:
<221> NAME/KEY: MISC_FEATURE
<222> LOCATION: (1)..(883)
<223> OTHER INFORMATION: C125S, C347S, C492S, C515S, C723S, C839S,
      V426L, V650L, A702V, V795I variant of T7 DNA-dependent RNA
      polymerase, amino acid sequence including N-terminal methionine;
      corresponding to #36 in Table 3

<400> SEQUENCE: 72

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val

```
                50                  55                  60
Ala Asp Asn Ala Ala Lys Pro Leu Ile Thr Thr Leu Leu Pro Lys
65                  70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Ser Leu Thr Ser
                115                 120                 125

Ala Asp Asn Thr Thr Val Gln Ala Val Ala Ser Ala Ile Gly Arg Ala
                130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Ser Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480
```

```
Phe Ile Glu Glu Asn His Glu Asn Ile Met Ala Ser Ala Lys Ser Pro
            485                 490                 495
Leu Glu Asn Thr Trp Trp Ala Glu Gln Asp Ser Pro Phe Cys Phe Leu
        500                 505                 510
Ala Phe Ser Phe Glu Tyr Ala Gly Val Gln His His Gly Leu Ser Tyr
    515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Leu Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Val Ala Lys
    690                 695                 700
Leu Leu Ala Ala Glu Val Lys Asp Lys Lys Thr Gly Glu Ile Leu Arg
705                 710                 715                 720
Lys Arg Ser Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Ile Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Ser Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala
```

```
<210> SEQ ID NO 73
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: DNA encoding N-terminal Histidine (His6) tag
      with linker sequence, fused to the first two N-terminal amino
      acids of T7 (Met and Asn)
<220> FEATURE:
<221> NAME/KEY: misc_feature
<222> LOCATION: (28)..(33)
<223> OTHER INFORMATION: codons encoding the first two T7 amino acids
      Met and Asn
<220> FEATURE:
<221> NAME/KEY: misc_feature
<222> LOCATION: (31)..(33)
<223> OTHER INFORMATION: codon corresponding to positions 4 to 6 in each
      of SEQ ID NOs: 1, 3, 5, 7, 9, 11, 13, 15, 17, 19, 21, 23, 25, 27,
      29, 31, 33, 35, 37, 39, 41, 43, 45, 47, 49, 51, 53, 55, 57, 59,
      61, 63, 65, 67, 69, 71

<400> SEQUENCE: 73
atgcatcacc atcatcacca cggatccatg aac                                    33

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Amino acid sequence of N-terminal Histidine
      (His6) tag with linker sequence, fused to the first two N-terminal
      amino acids of T7 (Met and Asn)
<220> FEATURE:
<221> NAME/KEY: MISC_FEATURE
<222> LOCATION: (1)..(11)
<223> OTHER INFORMATION: Amino acid Asn corresponding to Asn on position
      2 of each of SEQ ID NOs: 2, 4, 6, 8, 10, 12, 14, 16, 18, 20, 22,
      24, 26, 28, 30, 32, 34, 36, 38, 40, 42, 44, 46, 48, 50, 52, 54,
      56, 58, 60, 62, 64, 66, 68, 70, 72
<220> FEATURE:
<221> NAME/KEY: MISC_FEATURE
<222> LOCATION: (2)..(7)
<223> OTHER INFORMATION: Histidine-tag (His6)
<220> FEATURE:
<221> NAME/KEY: MISC_FEATURE
<222> LOCATION: (8)..(9)
<223> OTHER INFORMATION: Linker sequence

<400> SEQUENCE: 74

Met His His His His His His Gly Ser Met Asn
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic His tag
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: MISC_FEATURE
<222> LOCATION: (1)..(7)
<223> OTHER INFORMATION: This region may encompass 3 to 7 "His" residues

<400> SEQUENCE: 75
```

```
His His His His His His His
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic 6xHis (His6) tag

<400> SEQUENCE: 76

His His His His His His
1               5
```

T7 RNA POLYMERASE VARIANTS WITH CYSTEINE-SERINE SUBSTITUTIONS

PRIORITY CLAIM

This application is a continuation of U.S. patent application Ser. No. 13/436,110 filed Mar. 30, 2012, which claims the benefit of European Patent Application No 11160799.0, filed Apr. 1, 2011, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 28, 2012, is named SEQUENCE_LISTING_27368 US.txt, and is 425,986 bytes in size.

FIELD OF THE DISCLOSURE

The present disclosure pertains generally to the fields of molecular biology and protein biochemistry. More particularly, the instant disclosure pertains to the field of enzyme engineering.

BACKGROUND OF THE DISCLOSURE

T7 RNA polymerase (E.C. 2.7.7.6.), also referred to herein as "T7 polymerase" or "T7," is a monomeric bacteriophage encoded DNA directed RNA polymerase which catalyzes the formation of RNA in the 5'→3' direction. In the process of initiation of transcription, T7 recognizes a specific promoter sequence, the T7 promoter. T7 consists of 883 amino acids and has a molecular weight of 99 kDa. At the amino acid sequence level, T7 is highly homologous to T3 RNA polymerase and, to a lesser extent, SP6 RNA polymerase. The three-dimensional structure of T7 is also similar to other polymerases with different template and substrate specificities, despite low sequence similarity. T7 consists of different domains, the N-terminal domain, the "thumb", the "palm" and the "fingers" (as described in Sousa, R., and Mukherjee, S., Prog. Nucl. Acid Res. Mol. Biol. 73 (2003) 1-41).

Cloning and expression of the gene encoding T7 has been described in literature (see, U.S. Pat. No. 4,952,496, the disclosure of which is expressly incorporated by reference). Conformational changes of T7 during transcription (see, Ma, K., et. al., Proc. Nat. Acad. Sci. 102 (2005) 17612-17617), the facilitation of promoter clearance of T7 (see, Guillerez, J., et al., Proc. Natl. Acad. Sci. 102 (2005) 5958-5963) and the abortive cycling phenomenon of T7 (see, He, B., et al., J. Mol. Biol. 265 (1997) 275-288) have all been studied.

T7 has been classified as having high promoter specificity and RNA polymerase enzymatic activity, and as being useful for a variety of applications in molecular biology. In the field of recombinant protein expression, T7 is used for the high-level expression of recombinant genes in E. coli (for example, as discussed in Studier, F. W., and Moffat, B. A., J. Mol. Biol. 189 (1986) 113-130). The synthesis of defined oligoribonucleotides was described by Milligan, J. F., et al., Nucl. Aids Res. 15 (1987) 8783-8798. However, for at least some applications with which T7 RNA Polymerase may be utilized a more stable T7 RNA polymerase would be of value.

SUMMARY OF THE DISCLOSURE

According to the instant invention, novel variants of T7 polymerase are provided. According to embodiments of the invention, a T7 variant is provided which includes a Cysteine-Serine substitution on position 723 of the amino acid sequence of the T7 polypeptide. According to some embodiments, a T7 variant has a DNA-dependent RNA polymerase enzymatic activity and a reduced tendency to form intermolecular homodimers by way of oxidizing thiol groups is provided. The amino acid substitutions, according to the instant invention, have none (or at most only minimal) impact on the RNA polymerase activity of the T7 polypeptide. According to the instant disclosure, the mutations disclosed herein can optionally be combined with even further mutations, including mutations which provide enhanced thermostability compared to the wild-type reference.

According to embodiments of the present disclosure, variants of T7 RNA polymerase with Cys-Ser substitution mutations leading to improved stability are provided. Further, the instant disclosure provides combinations of several T7 RNA polymerase mutations in a single T7 variant (double-, triple-, quadruple-, multiple-mutant), with the proviso that the combined mutations lead to an even increased stability, that is to say enhanced storage characteristics. Even further, the present invention provides mutations which give rise to T7 variants which additionally exhibit enhanced stability in thermal unfolding assays.

The present invention also provides improved variants of T7 RNA polymerase by introducing mutations which reduce one or more thiol (=mercapto, =—SH, =sulfhydryl) group(s) of the enzyme while retaining enzymatic activity. For example, some embodiments of the instant disclosure include amino acid substitutions with Serine at any of the positions Cys125, Cys347, Cys492, Cys515, Cys723, Cys839, and combinations thereof.

According to some embodiments of the instant disclosure, an aqueous solution lacking a reducing agent with a thiol group is provided. The aqueous solution comprises a variant polypeptide of T7 RNA polymerase which has DNA-dependent RNA polymerase activity and a different amino acid sequence from SEQ ID NO.:2. The variant also includes a Cysteine residue at amino acid position between 510 and 530, the numbering being from the N-terminus of SEQ ID NO.:2. Further, the variant includes a Serine residue substitution for the Cysteine residue at amino acid position 723, again numbered from the N-terminus of SEQ ID NO.:2. Even further, in the aqueous solution the variant lacks homomultimer formation of intermolecular disulfide bonds.

According to some such embodiments, the variant may also include one or more of the Cysteine-Serine substitutions selected from the group consisting of Cys125Ser, Cys347Ser, Cys492Ser, Cys515Ser, and Cys839Ser.

According to other such embodiments, the variant may also include one or more of the amino acid substitutions selected from the group consisting of Val426Leu, Val426Ile, Val426Phe, Ser633Val, Ser633Met, Val650Leu, Thr654Leu, Ala702Val, and Val795Ile.

Another embodiment of the instant disclosure includes a method of synthesizing a RNA molecule. Embodiments of this method include the step of providing an aqueous solution devoid of a reducing agent with a thiol group. The solution has a variant polypeptide of T7 RNA polymerase. The variant also has DNA-dependent RNA polymerase activity and an amino acid sequence different from SEQ ID NO:2. Further, the variant is devoid of homomultimer formation of intermolecular disulfide bonds when in the solution. Embodiments of this method also include the step of providing a template DNA molecule comprising a T7 promoter functionally linked to a target nucleotide sequence to be transcribed. Embodiments of this method also include the steps of contacting, within the solution, the template DNA molecule with the variant in the presence of ribonucleoside triphosphates, and incubating the solution, following the step of contacting, under conditions favoring RNA polymerase activity, thereby synthesizing the RNA molecule.

According to some such embodiments, the variant may also include one or more of the Cysteine-Serine substitutions selected from the group consisting of Cys125Ser, Cys347Ser, Cys492Ser, Cys515Ser, and Cys839Ser.

According to other such embodiments, the variant may also include one or more of the amino acid substitutions selected from the group consisting of Val426Leu, Val426Ile, Val426Phe, Ser633Val, Ser633Met, Val650Leu, Thr654Leu, Ala702Val, and Val795Ile.

According to yet other embodiments of the instant disclosure, a method of producing an aqueous solution devoid of a reducing agent including a thiol group is provided. According to such embodiments, the solution comprises a variant of T7 RNA polymerase having DNA-dependent RNA polymerase activity and an amino acid sequence different from SEQ ID NO:2. The variant is devoid of homomultimer formation of intermolecular disulfide bonds when in the solution. According to such embodiments, the method comprises the step of providing the variant by substituting a Cysteine residue at amino acid position 723, the positions numbered from the N-terminus of SEQ ID NO.:2, with a Serine residue. Such embodiments also include the steps of reverse-transcribing the amino acid sequence of the variant, thereby obtaining a nucleotide sequence encoding the variant. Such embodiments also include the step of expressing a nucleic acid molecule comprising the nucleotide sequence of the variant obtained in the step of reverse transcribing in an expression system, thereby expressing a polypeptide, and purifying the polypeptide expressed in the step of expressing, by way of chromatography using an aqueous mobile phase devoid of a reducing agent including a thiol group, thereby obtaining the solution with the variant.

According to some such embodiments, the variant may also include one or more of the Cysteine-Serine substitutions selected from the group consisting of Cys125Ser, Cys347Ser, Cys492Ser, Cys515Ser, and Cys839Ser.

According to other such embodiments, the variant may also include one or more of the amino acid substitutions selected from the group consisting of Val426Leu, Val426Ile, Val426Phe, Ser633Val, Ser633Met, Val650Leu, Thr654Leu, Ala702Val, and Val795Ile.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 3 is a stained SDS polyacrylamide gel (following electrophoresis) having: wild-type T7 RNA polymerase without His-tag ((Lane 1); wild-type T7 RNA polymerase including His6-tag (Lane 2); T7 variant #8 [Cys125Ser, Cys347Ser, Cys492Ser, Cys515Ser, Cys723Ser, Cys839Ser] including His6-tag (Lane 3); T7 variant #6 [Cys723Ser] including His6-tag (Lane 4); T7 variant #3 [Cys347Ser] including His6-tag (Lane 5); T7 variant #7 [Cys839Ser] including His6-tag (Lane 6); T7 variant #2 [Cys125Ser] including His6-tag (Lane 7); T7 variant #4 [Cys492Ser] including His6-tag (Lane 8); and T7 variant #5 [Cys515Ser] including His6-tag (Lane 9), in which 10 mM DTT was added prior to electrophoresis to provide reducing conditions.

Figure 1:
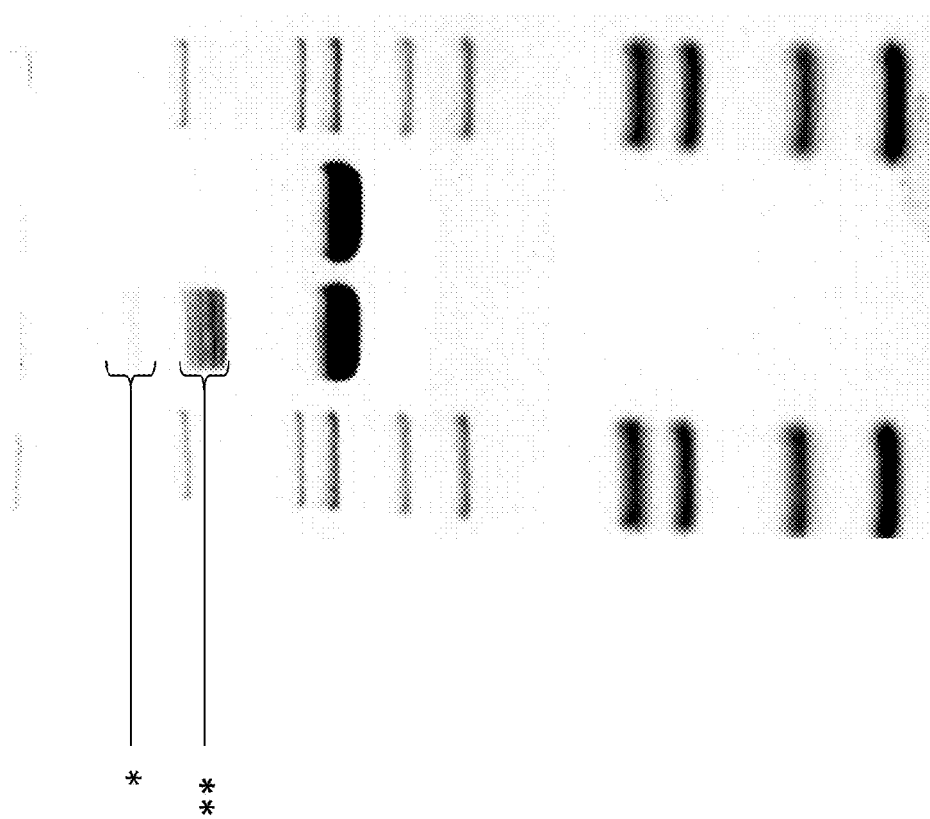
FIG. 1 is a stained SDS polyacrylamide gel (following electrophoresis) having wild-type T7 RNA polymerase in both lanes 1 and 2, the T7 RNA polymerase of lane 2 was treated with reducing reagents (DTT).

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO.: 1 is the DNA sequence encoding wild-type T7 DNA-dependent RNA polymerase, including start codon encoding N-terminal methionine; corresponding to #1 in Table 3.

SEQ ID NO.: 2 is the wild-type T7 DNA-dependent RNA polymerase, amino acid sequence including N-terminal methionine; corresponding to #1 in Table 3.

SEQ ID NO.: 3 is the DNA sequence encoding the Cys125Ser variant of T7 DNA-dependent RNA polymerase, including start codon encoding N-terminal methionine; corresponding to #2 in Table 3.

SEQ ID NO.: 4 is the sequence of Cys125Ser variant of T7 DNA-dependent RNA polymerase, amino acid sequence including N-terminal methionine; corresponding to #2 in Table 3.

SEQ ID NO.: 5 is the DNA sequence encoding the Cys347Ser variant of T7 DNA-dependent RNA polymerase, including start codon encoding N-terminal methionine; corresponding to #3 in Table 3.

SEQ ID NO.: 6 is the Cys347Ser variant of T7 DNA-dependent RNA polymerase, amino acid sequence including N-terminal methionine; corresponding to #3 in Table 3.

SEQ ID NO.: 7 is the DNA sequence encoding the Cys492Ser variant of T7 DNA-dependent RNA polymerase, including start codon encoding N-terminal methionine; corresponding to #4 in Table 3.

SEQ ID NO.: 8 is Cys492Ser variant of T7 DNA-dependent RNA polymerase, amino acid sequence including N-terminal methionine; corresponding to #4 in Table 3.

SEQ ID NO.: 9 is the DNA sequence encoding the Cys515Ser variant of T7 DNA-dependent RNA polymerase, including start codon encoding N-terminal methionine; corresponding to #5 in Table 3.

SEQ ID NO.: 10 is Cys515Ser variant of T7 DNA-dependent RNA polymerase, amino acid sequence including N-terminal methionine; corresponding to #5 in Table 3.

SEQ ID NO.: 11 is the DNA sequence encoding the Cys723Ser variant of T7 DNA-dependent RNA polymerase, including start codon encoding N-terminal methionine; corresponding to #6 in Table 3.

SEQ ID NO.: 12 is the Cys723Ser variant of T7 DNA-dependent RNA polymerase, amino acid sequence including N-terminal methionine; corresponding to #6 in Table 3.

SEQ ID NO.: 13 is the DNA sequence encoding the Cys839Ser variant of T7 DNA-dependent RNA polymerase, including start codon encoding N-terminal methionine; corresponding to #7 in Table 3.

SEQ ID NO.: 14 is Cys839Ser variant of T7 DNA-dependent RNA polymerase, amino acid sequence including N-terminal methionine; corresponding to #7 in Table 3.

SEQ ID NO.: 15 is the DNA sequence encoding the Cys125Ser, Cys347Ser, Cys492Ser, Cys515Ser, Cys723Ser, Cys839Ser variant of T7 DNA-dependent RNA polymerase, including start codon encoding N-terminal methionine; corresponding to #8 in Table 3.

SEQ ID NO.: 16 is Cys125Ser, Cys347Ser, Cys492Ser, Cys515Ser, Cys723Ser, Cys839Ser variant of T7 DNA-dependent RNA polymerase, amino acid sequence including N-terminal methionine; corresponding to #8 in Table 3.

SEQ ID NO.: 17 is the DNA sequence encoding the Val426Leu variant of T7 DNA-dependent RNA polymerase, including start codon encoding N-terminal methionine; corresponding to #9 in Table 3.

SEQ ID NO.: 18 is Val426Leu variant of T7 DNA-dependent RNA polymerase, amino acid sequence including N-terminal methionine; corresponding to #9 in Table 3.

SEQ ID NO.: 19 is the DNA sequence encoding the Cys723Ser, Val426Leu variant of T7 DNA-dependent RNA polymerase, including start codon encoding N-terminal methionine; corresponding to #10 in Table 3.

SEQ ID NO.: 20 is Cys723Ser, Val426Leu variant of T7 DNA-dependent RNA polymerase, amino acid sequence including N-terminal methionine; corresponding to #10 in Table 3.

SEQ ID NO.: 21 is the DNA sequence encoding the Val426Ile variant of T7 DNA-dependent RNA polymerase, including start codon encoding N-terminal methionine; corresponding to #11 in Table 3.

SEQ ID NO.: 22 is Val426Ile variant of T7 DNA-dependent RNA polymerase, amino acid sequence including N-terminal methionine; corresponding to #11 in Table 3.

SEQ ID NO.: 23 is the DNA sequence encoding the Cys723Ser, Val426Ile variant of T7 DNA-dependent RNA polymerase, including start codon encoding N-terminal methionine; corresponding to #12 in Table 3.

SEQ ID NO.: 24 is Cys723Ser, Val426Ile variant of T7 DNA-dependent RNA polymerase, amino acid sequence including N-terminal methionine; corresponding to #12 in Table 3.

SEQ ID NO.: 25 is the DNA sequence encoding the Val426Phe variant of T7 DNA-dependent RNA polymerase, including start codon encoding N-terminal methionine; corresponding to #13 in Table 3.

SEQ ID NO.: 26 is Val426Phe variant of T7 DNA-dependent RNA polymerase, amino acid sequence including N-terminal methionine; corresponding to #13 in Table 3.

SEQ ID NO.: 27 is the DNA sequence encoding the Cys723Ser, Val426Phe variant of T7 DNA-dependent RNA polymerase, including start codon encoding N-terminal methionine; corresponding to #14 in Table 3.

SEQ ID NO.: 28 is Cys723Ser, Val426Phe variant of T7 DNA-dependent RNA polymerase, amino acid sequence including N-terminal methionine; corresponding to #14 in Table 3.

SEQ ID NO.: 29 is the DNA sequence encoding the Ser633Met variant of T7 DNA-dependent RNA polymerase, including start codon encoding N-terminal methionine; corresponding to #15 in Table 3.

SEQ ID NO.: 30 is Ser633Met variant of T7 DNA-dependent RNA polymerase, amino acid sequence including N-terminal methionine; corresponding to #15 in Table 3.

SEQ ID NO.: 31 is the DNA sequence encoding the Cys723Ser, Ser633Met variant of T7 DNA-dependent RNA polymerase, including start codon encoding N-terminal methionine; corresponding to #16 in Table 3.

SEQ ID NO.: 32 is the DNA sequence encoding the Cys723Ser, Ser633Met variant of T7 DNA-dependent RNA polymerase, including start codon encoding N-terminal methionine; corresponding to #16 in Table 3.

SEQ ID NO.: 33 is the DNA sequence encoding the Val650Leu variant of T7 DNA-dependent RNA polymerase, including start codon encoding N-terminal methionine; corresponding to #17 in Table 3.

SEQ ID NO.: 34 is Val650Leu variant of T7 DNA-dependent RNA polymerase, amino acid sequence including N-terminal methionine; corresponding to #17 in Table 3.

SEQ ID NO.: 35 is the DNA sequence encoding the Cys723Ser, Val650Leu variant of T7 DNA-dependent RNA polymerase, including start codon encoding N-terminal methionine; corresponding to #18 in Table 3.

SEQ ID NO.: 36 is Cys723Ser, Val650Leu variant of T7 DNA-dependent RNA polymerase, amino acid sequence including N-terminal methionine; corresponding to #18 in Table 3.

SEQ ID NO.: 37 is the DNA sequence encoding the Thr654Leu variant of T7 DNA-dependent RNA polymerase, including start codon encoding N-terminal methionine; corresponding to #19 in Table 3.

SEQ ID NO.: 38 is Thr654Leu variant of T7 DNA-dependent RNA polymerase, amino acid sequence including N-terminal methionine; corresponding to #19 in Table 3.

SEQ ID NO.: 39 is the DNA sequence encoding the Cys723Ser, Thr654Leu variant of T7 DNA-dependent RNA polymerase, including start codon encoding N-terminal methionine; corresponding to #20 in Table 3.

SEQ ID NO.: 40 is Cys723Ser, Thr654Leu variant of T7 DNA-dependent RNA polymerase, amino acid sequence including N-terminal methionine; corresponding to #20 in Table 3.

SEQ ID NO.: 41 is the DNA sequence encoding the Ala702Val variant of T7 DNA-dependent RNA polymerase, including start codon encoding N-terminal methionine; corresponding to #21 in Table 3.

SEQ ID NO.: 42 is Ala702Val variant of T7 DNA-dependent RNA polymerase, amino acid sequence including N-terminal methionine; corresponding to #21 in Table 3.

SEQ ID NO.: 43 is the DNA sequence encoding the Cys723Ser, Ala702Val variant of T7 DNA-dependent RNA polymerase, including start codon encoding N-terminal methionine; corresponding to #22 in Table 3.

SEQ ID NO.: 44 is Cys723Ser, Ala702Val variant of T7 DNA-dependent RNA polymerase, amino acid sequence including N-terminal methionine; corresponding to #22 in Table 3.

SEQ ID NO.: 45 is the DNA sequence encoding the Val795Ile variant of T7 DNA-dependent RNA polymerase, including start codon encoding N-terminal methionine; corresponding to #23 in Table 3.

SEQ ID NO.: 46 is Val795Ile variant of T7 DNA-dependent RNA polymerase, amino acid sequence including N-terminal methionine; corresponding to #23 in Table 3.

SEQ ID NO.: 47 is the DNA sequence encoding the Cys723Ser, Val795Ile variant of T7 DNA-dependent RNA polymerase, including start codon encoding N-terminal methionine; corresponding to #24 in Table 3.

SEQ ID NO.: 48 is Cys723Ser, Val795Ile variant of T7 DNA-dependent RNA polymerase, amino acid sequence including N-terminal methionine; corresponding to #24 in Table 3.

SEQ ID NO.: 49 is the DNA sequence encoding the Ala702Val, Val795Ile variant of T7 DNA-dependent RNA polymerase, including start codon encoding N-terminal methionine; corresponding to #25 in Table 3.

SEQ ID NO.: 50 is Ala702Val, Val795Ile variant of T7 DNA-dependent RNA polymerase, amino acid sequence including N-terminal methionine; corresponding to #25 in Table 3.

SEQ ID NO.: 51 is the DNA sequence encoding the Cys723Ser, Ala702Val, Val795Ile variant of T7 DNA-dependent RNA polymerase, including start codon encoding N-terminal methionine; corresponding to #26 in Table 3.

SEQ ID NO.: 52 is Cys723Ser, Ala702Val, Val795Ile variant of T7 DNA-dependent RNA polymerase, amino acid sequence including N-terminal methionine; corresponding to #26 in Table 3.

SEQ ID NO.: 53 is the DNA sequence encoding the Val426Leu, Ala702Val variant of T7 DNA-dependent RNA polymerase, including start codon encoding N-terminal methionine; corresponding to #27 in Table 3.

SEQ ID NO.: 54 is Val426Leu, Ala702Val variant of T7 DNA-dependent RNA polymerase, amino acid sequence including N-terminal methionine; corresponding to #27 in Table 3.

SEQ ID NO.: 55 is the DNA sequence encoding the Cys723Ser, Val426Leu, Ala702Val variant of T7 DNA-dependent RNA polymerase, including start codon encoding N-terminal methionine; corresponding to #28 in Table 3.

SEQ ID NO.: 56 is Cys723Ser, Val426Leu, Ala702Val variant of T7 DNA-dependent RNA polymerase, amino acid sequence including N-terminal methionine; corresponding to #28 in Table 3.

SEQ ID NO.: 57 is the DNA sequence encoding the Val426Leu, Val795Ile variant of T7 DNA-dependent RNA polymerase, including start codon encoding N-terminal methionine; corresponding to #29 in Table 3.

SEQ ID NO.: 58 is Val426Leu, Val795Ile variant of T7 DNA-dependent RNA polymerase, amino acid sequence including N-terminal methionine; corresponding to #29 in Table 3.

SEQ ID NO.: 59 is the DNA sequence encoding the Cys723Ser, Val426Leu, Val795Ile variant of T7 DNA-dependent RNA polymerase, including start codon encoding N-terminal methionine; corresponding to #30 in Table 3.

SEQ ID NO.: 60 is the DNA sequence encoding the Cys723Ser, Val426Leu, Val795Ile variant of T7 DNA-dependent RNA polymerase, including start codon encoding N-terminal methionine; corresponding to #30 in Table 3.

SEQ ID NO.: 61 is the DNA sequence encoding the Val426Leu, Ala702Val, Val795Ile variant of T7 DNA-dependent RNA polymerase, including start codon encoding N-terminal methionine; corresponding to #31 in Table 3.

SEQ ID NO.: 62 is Val426Leu, Ala702Val, Val795Ile variant of T7 DNA-dependent RNA polymerase, amino acid sequence including N-terminal methionine; corresponding to #31 in Table 3.

SEQ ID NO.: 63 is the DNA sequence encoding the Cys723Ser, Val426Leu, Ala702Val, Val795Ile variant of T7 DNA-dependent RNA polymerase, including start codon encoding N-terminal methionine; corresponding to #32 in Table 3.

SEQ ID NO.: 64 is Cys723Ser, Val426Leu, Ala702Val, Val795Ile variant of T7 DNA-dependent RNA polymerase, amino acid sequence including N-terminal methionine; corresponding to #32 in Table 3.

SEQ ID NO.: 65 is the DNA sequence encoding the Cys125Ser, Cys347Ser, Cys492Ser, Cys515Ser, Cys723Ser, Cys839Ser, Val426Leu, Ala702Val, Val795Ile variant of T7 DNA-dependent RNA polymerase, including start codon encoding N-terminal methionine; corresponding to #33 in Table 3.

SEQ ID NO.: 66 is Cys125Ser, Cys347Ser, Cys492Ser, Cys515Ser, Cys723Ser, Cys839Ser, Val426Leu, Ala702Val, Val795Ile variant of T7 DNA-dependent RNA polymerase, amino acid sequence including N-terminal methionine; corresponding to #33 in Table 3.

SEQ ID NO.: 67 is the DNA sequence encoding the Val426Leu, Val650Leu, Ala702Val, Val795Ile variant of T7 DNA-dependent RNA polymerase, including start codon encoding N-terminal methionine; corresponding to #34 in Table 3.

SEQ ID NO.: 68 is Val426Leu, Val650Leu, Ala702Val, Val795Ile variant of T7 DNA-dependent RNA polymerase, amino acid sequence including N-terminal methionine; corresponding to #34 in Table 3.

SEQ ID NO.: 69 is the DNA sequence encoding the Cys723Ser, Val426Leu, Val650Leu, Ala702Val, Val795Ile variant of T7 DNA-dependent RNA polymerase, including start codon encoding N-terminal methionine; corresponding to #35 in Table 3.

SEQ ID NO.: 70 is Cys723Ser, Val426Leu, Val650Leu, Ala702Val, Val795Ile variant of T7 DNA-dependent RNA polymerase, amino acid sequence including N-terminal methionine; corresponding to #35 in Table 3 SEQ ID NO.: 71 is the DNA sequence encoding the C125S, C347S, C492S, C515S, C723S, C839S, V426L, V650L, A702V, V795I variant of T7 DNA-dependent RNA polymerase, including start codon encoding N-terminal methionine; corresponding to #36 in Table 3.

SEQ ID NO.: 72 is C125S, C347S, C492S, C515S, C723S, C839S, V426L, V650L, A702V, V795I variant of T7 DNA-dependent RNA polymerase, amino acid sequence including N-terminal methionine; corresponding to #36 in Table 3.

SEQ ID NO.: 73 is the DNA encoding N-terminal Histidine (His6) tag with linker sequence, fused to the first two N-terminal amino acids of T7 (Met and Asn).

SEQ ID NO.: 74 is the Amino acid sequence of N-terminal Histidine (His6) tag with linker sequence, fused to the first two N-terminal amino acids of T7 (Met and Asn).

SEQ ID NO.: 75 is the Histidine tag (amino acids); this region may encompass 3 to 7 "His" residues.

SEQ ID NO.: 76 is the His6 tag (amino acids).

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The instant disclosure provides the surprising and unexpected discovery that the T7 RNA polymerase Cys-Ser mutations disclosed herein do not impact equally on intramolecular disulfide bond formation of T7 polymerase. Further, in embodiments of the instant disclosure it is disclosed herein that, surprisingly, Cys723 is an important residue with regards to homomultimer formation. Further, in some embodiments Cys839 may be involved in forming disulfide bridges in homomultimers. For example, according to some embodiments of the instant disclosure, a T7 variant with only a Cys723Ser substitution, homomultimer formation is detectably absent. According to an embodiment of the instant disclosure, a T7 variant with only a C839S substitution homomultimer formation is substantially reduced. Very surprisingly, according to another embodiment of the instant disclosure, a sextuple amino acid substitution T7 variant [C125S, C347S, C492S, C515S, C723S, C839S] is indistinguishable from a T7 variant with only a C723S substitution, as far as homomultimer formation is concerned. Also surprising, the sextuple T7 variant disclosed herein and the T7 variants with only a C723S substitution or only a C839S substitution exhibit RNA polymerase activity similar to that of the wild-type T7 enzyme. As disclosed herein, amino acid substitution mutations on the positions C125, C347, C492, C515, C723, and C839 are very useful and advantageous for constructing variant T7 polymerase enzymes with reduced tendency to form multimers with disulfide bridges.

The formation of disulfide bonds can occur during or after the synthesis of certain proteins. Intramolecular disulfide bonds can significantly contribute to the stability of proteins. Disulfide bond formation also occurs between different protein molecules. Cysteine residues involved in this process have to be located at the surface of the protein molecule and have to be solvent exposed. Additionally, the cysteine residues have to be in a suitable geometry and distance to each other to facilitate the formation of a disulfide bond.

By way of forming one or more intermolecular disulfide bond(s) between proteins, di-, tri-, tetra-, penta-, and higher degree of multimeric protein complexes can be generated. However, uncontrolled and unfavourable formation of such protein complexes by disulfide bonds under artificial conditions (e.g. in purified preparations of proteins) can impact on biological (e.g. enzymatic) activity or functionality. Therefore, efforts are made to keep proteins under reducing conditions. A common method is the addition of reducing agents to the storage buffers; examples for such reducing agents are mercaptoethanol, dithiothreitol (DTT), dithioerythritol (DTE) and others. However, thiol group reducing agents have a limited shelf life as they themselves are oxidized by molecular oxygen. As a consequence, thiol reducing agents are losing their protective activity over time, and oxidation of cysteine residues together with disulfide bond formation can again take place.

If a protein sample contains a mixture of different polypeptides or if the sample is a crude extract, formation of multimers is possible between molecules of different protein species (heteromultimers). If the mixture contains several purified polypeptides of defined activities, formation of heteromultimers between these proteins can negatively influence such activities, affecting single polypeptides separately or all members of the sample.

According to the instant disclosure, T7 RNA polymerase (such as the wild-type T7 RNA polymerase) contains 12 cysteines each having free thiol as functional group. When the thiol groups of two cysteine residues are brought near each other, an oxidation reaction can generate a cystine unit with a disulfide bond (—S—S—). Storage of T7 RNA polymerase in the absence of thiol reducing agents results in reduced enzymatic activity. Reduction of activity is correlated with the formation of dimers, trimers and even multimers of the enzyme. The kinetics of disulfide bond formation are strongly dependent on parameters like protein concentration, reaction time, temperature and the presence or absence of oxidizing reagents. Therefore, in practice, the percentage of multimers present in a sample can vary depending on the origin, age and composition of the sample. Even during the purification procedure intermolecular disulfide bond formation can be observed sometimes.

T7 multimers such as dimers, trimers or even higher degree multimers, may exhibit decreased polymerase activity, possibly due to a reduced accessibility of the active sites. A reduced flexibility of the individual polypeptide backbones could also negatively impact enzymatic function. Although polymerase activity can be restored by adding freshly prepared —SH reagents, it is required to continuously monitor residual activity of the enzyme. In order to safeguard and/or regain enzymatic activity and/or provide an enzyme preparation with defined T7 polymerase activity, it is further necessary to frequently manipulate the material, for example by removing and analyzing samples and reacting T7 preparations with reducing agents, etc.

DTNB [5,5'-dithiobis-(2-nitrobenzoic acid), also known as Ellman's reagent] is a chemical which can be used to quantify the number or concentration of thiol groups in a polypeptide. A thiol group reacts with DTNB, cleaving the disulfide bond to give 2-nitro-5-thiobenzoate ($NTB^-$), which ionizes to the $NTB^{2-}$ dianion in water at neutral and alkaline pH. The $NTB^{2-}$ ion has a yellow color and can be determined, for example, spectrophotometrically. The reaction of thiol groups and DTNB is rapid and stoichiometric, with one mole of thiol releasing one mole of NTB (for example, the reactivity of T7 RNA polymerase with DTNB has been previously determined as disclosed in Mukherjee, S., et al., Cell 110 (2002) 81-91). Per one native polypeptide of wild-type T7 polymerase enzyme the equivalent of about 2 reactive Cys residues were found but for the denatured wild-type T7 enzyme the number of reactive Cys residues determined was 12.

According to the instant disclosure, in at least some applications with which T7 RNA Polymerase may be utilized, such as in vitro transcription and in vitro amplification methods including Nucleic Acid Sequence Based Amplification ("NASBA"), Transcription mediated amplification ("TMA"), and other related methods and applications, increasing the stability of the T7 RNA polymerase would be beneficial. For example, it would be beneficial to have a T7 RNA polymerase with an increased storage time wherein any loss of polymerase enzymatic activity is minimized and/or a T7 RNA polymerase which can be stored at room temperature with only minor or no loss of enzymatic activity. Also, combining the technical features leading to enhanced storage characteristics with other features leading to enhanced thermostability (e.g., higher reaction temperatures of isothermal amplification) could allow the amplification of RNA having secondary structures. It has also been shown with the polymerase chain reaction (PCR) technology that high annealing temperatures allow the specific hybridization of a primer to its target resulting in a highly specific amplification. With the same advantage, more thermostable enzymes could in principle also be applied to isothermal amplifications.

According to some embodiments of the instant disclosure, a T7 RNA polymerase variant having improved stability, for example enhanced storage characteristics and a reduced tendency to form multimers with disulfide bridges, is provided. According to some embodiments, the T7 RNA polymerase variants provided herein combine the enhanced stability features with polymerase activity at reaction temperatures higher than those of the wild-type T7 enzyme.

According to the present disclosure, Cys723 is a cysteine residue of T7 polymerase which contributes to disulfide bond formation. For example, according to the instant disclosure, Cys723Ser variants, even after long term storage of such purified variants, analysis by way of SDS gel electrophoresis reveals only a single band under non-reducing conditions. This indicates that the homodimer formation is completely suppressed by the introduction of this single specific mutation. No other Cys-Ser substitution was found to produce a similar effect in a T7 variant with RNA polymerase activity, i.e. in an active enzyme.

As also disclosed herein, the combination of six mutations within a T7 gene results in an active enzyme. The six-fold mutant (Cys125Ser, Cys347Ser, Cys492Ser, Cys515Ser, Cys723Ser, Cys839Ser) also shows a single band under non-reducing conditions (and reducing conditions, too). This indicates that dimer formation can be suppressed completely by the introduction of Cys-Ser substitution mutations according to the invention.

The present invention provides novel variants of T7 polymerase, variants which are characterized by a different composition of amino acids compared to the wild-type T7 RNA polymerase polypeptide (wild-type reference). Such a "variant" is an allelic form of the wild-type T7 protein, wherein the T7 variant is generated by way of amino acid substitution. A T7 variant according to the invention is further characterized by a DNA-dependent RNA polymerase enzymatic activity, and a reduced tendency to form intramolecular dimers by way of oxidizing thiol groups. The identified amino acid substitutions according to the invention appear to impact only minimally, if at all, on the biological function of the T7 polymerase polypeptide, including RNA polymerase activity. The mutations can optionally be combined with even further mutations, including mutations which provide enhanced thermostability compared to the wild-type reference.

Certain terms are used with particular meaning or are defined for the first time in this description of the present invention. For the purposes of the invention, the terms used are defined by their art-accepted definitions, when such exist, except that when those definitions conflict or partially conflict with the definitions set forth below. In the event of a conflict in definition, the meaning of a term is first defined by any of the definitions set forth in this document.

The term "comprising" is used in the description of the invention and in the claims to mean "including, but not necessarily limited to".

The articles "a" and "an" are used herein to refer to one or to more than one (i.e. to "one or more" or "at least one") of the grammatical object of the article. By way of example, "an amino acid" means one amino acid or more than one amino acid.

If not stated otherwise, it is understood that the term "about" in combination with a numerical value n ("about n") indicates a value x in the interval given by the numerical value ±5% of the value, i.e. n−0.05*n≤x≤n+0.05*n. In case the term "about" in combination with a numerical value n describes a preferred embodiment of the invention, the value of n is most preferred, if not indicated otherwise.

A nucleotide sequence "encodes" a peptide or polypeptide when at least a portion of the nucleic acid, or its complement, can be directly translated to provide the amino acid sequence of the peptide or protein, or when the isolated nucleic acid can be used, alone or as part of an expression vector, to express the peptide or protein in vitro, in a prokaryotic host cell, or in a eukaryotic host cell.

Where a nucleotide sequence is single-stranded, it is to be understood that the complementary sequence of that nucleotide sequence is also included within the scope of the present invention.

The coding portion of a nucleotide sequence encoding a peptide or a polypeptide begins with a start codon encoding Methionine which thus becomes the N-terminal amino acid of the primary translation product. As part of post-translational processes, the N-terminal Methionine is frequently cleaved off, e.g. by a Methionine aminopeptidase which is a ubiquitous enzyme. In such a case, the primary translation product may give rise to a mixture comprising members without N-terminal Methionine and members retaining this amino acid as N-terminus. It is also possible that the form of the enzyme without N-terminal Methionine is the only one which can be isolated. However, the amino acid sequences of the wild-type T7 polymerase and the T7 variants according to the invention are described in the sequence listing including N-terminal Methionine. But the present invention also encompasses the T7 variants which do not include N-terminal Methionine.

For purposes of shorthand designation of T7 polymerase variants described herein, it is noted that for each mutation a number refers to the amino acid residue/position along the reference amino acid sequence of the wild-type T7 polymerase protein given in SEQ ID NO:2. Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, His H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine. An amino acid at a particular position in an amino acid sequence may be given by its three-letter abbreviation and a number. For example, "Cys723" or "C723" denote the Cysteine residue at amino acid position 723 in SEQ ID NO:2. In any T7 mutant and/or T7 variant disclosed herein, a substitution by a different amino acid may be given as the three-letter abbreviation added after the number indicating the position. For example, "Cys723Ser" (=[Cys723Ser]) or "C723S" (=[C723S]) denotes the substitution of Cysteine (Cys) at position 723 in SEQ ID NO:2 by Serine (Ser) (see #6 of Table 3). A Cys723Ser (=C723S) substitution results in an amino acid sequence as given in SEQ ID NO:12, encoded by the nucleotide sequence of SEQ ID NO:11. Exemplary further amino acid substitutions according to the instant disclosure are disclosed in Table 1a below (see Example 1). According to some embodiments, variants may include a plurality (for example 2 to 4) amino acid substitutions. Exemplary embodiments may include amino acid substitution combinations having one or more mutations as listed in Table 1a and Table 1b.

The term "polypeptide" or "protein" denotes a polymer composed of a plurality of amino acid monomers joined by peptide bonds. According to some embodiments, the polymer may comprise 50 or more monomers. For example, polypeptide or protein according to the instant invention comprises a T7 variant. A "peptide bond" is a covalent bond between a first amino acid and a second amino acid in which the α-amino group of the first amino acid is bonded to the α-carboxyl group of the second amino acid.

A "multimer" in the context of the present invention is understood as being a conjugate formed by covalently linking two or more (=a plurality of) members, each member being a polypeptide with one or more reactive and sterically accessible thiol groups (e.g. but not limited to Cys residues). After formation of the conjugate, two or more members are linked by at least one disulfide (—S—S—) bridge. Adjacent members are linked by one or more disulfide bridge(s), and members may be linked to other members by additional disulfide bridges. A conjugate with identical members (i.e. members of the same species of polypeptide) is also referred to as a homomultimer. Depending on the number of individual members linked in the conjugate, the multimer may be referred to as a dimer, trimer, tetramer, pentamer, hexamer, etc. A heteromultimer contains at least two different species of polypeptide.

A "reducing agent with a thiol group", also referred to as a "—SH reagent" denotes a reducing agent capable of preventing the formation of a disulfide bond of two —SH group-containing residues of one or more polypeptides. For example, according to the instant disclosure, the reducing agent with a thiol group is capable of preventing multimer formation of a T7 polypeptide with a further T7 polypeptide or the polypeptide of another species containing an —SH group. Exemplary —SH reagents within this definition include, but are not limited to, mercaptoethanol, dithiothreitol (DTT), dithioerythritol (DTE).

Illustrative T7 variants of the instant invention also comprise fusion proteins with an affinity tag such as, but not limited to, a Histidine tag (His-tag). A His-tag is an amino acid sequence containing several, for example, 3 to 7 consecutive Histidines. An illustrative embodiment of the instant disclosure include 6 consecutive Histidines. In a His-tag sequence the Histidines represent the essential portion. But facultatively there are few additional amino acids comprised in the His-tag. For example, a N-terminal T7 sequence including a His-tag can comprise the sequence N-Met His His His His His His Gly Ser-. For example, SEQ ID NO:74 comprises an illustrative embodiment of the instant disclosure including the foregoing amino acid sequence. In the present exemplary His-tag the amino acids Gly and Ser form a linker to the N-terminus of the T7 variant. The linker amino acids are part of the His-tag and typically arise as a cloning artifact of the nucleotide sequence encoding the His-tag (e.g. SEQ ID NO:73). The linker sequence in the His-tag may comprise 1 to 5 amino acids, for example, although the linker sequence may comprise greater than 5 amino acids.

According to embodiments of the instant invention, the N-terminal Methionine of a T7 variant may be replaced by a His-tag. Alternatively, the N-terminal sequence of the T7 variant, according to embodiments of the instant invention, may be extended by the His-tag. In such a case, the N-terminus of the primary translation product of the T7 variant comprises a N-terminal Methionine followed by the His-tag, followed by the Methionine encoded by the start codon of the original T7 encoding nucleotide sequence.

Purification of a His-tagged T7 wild-type or variant polypeptide may be efficiently performed by immobilized metal affinity chromatography, such as is employed in the purification of recombinant proteins containing a short affinity-tag consisting of Histidine residues (His-tag). Immobilized metal-affinity chromatography (described by Porath, J., et al., Nature 258 (1975) 598-599, for example) is based on the interaction between a transition metal ion ($Co^{2+}$, $Ni^{2+}$, $Cu^{2+}$, $Zn^{2+}$) immobilized on a particulate metal chelating affinity matrix and specific amino acid side chains. Histidine is the amino acid that exhibits the strongest interaction with immobilized metal ion matrices, as electron donor groups on the Histidine imidazole ring readily form coordination bonds with the immobilized transition metal.

A "vector" is a DNA which can comprise, i.e. carry, and maintain a DNA fragment according to the instant invention, including, for example, phages and plasmids. These terms are generally understood by those of skill in the art of genetic engineering for example. The term "expression cassette" denotes a nucleotide sequence encoding a pre-protein, operably linked to a promoter and a terminator. As for vectors containing an expression cassette, the terms "vector" and "expression vector" are used as synonyms.

The term "oligonucleotide" is used for a nucleic acid molecule, DNA (or RNA), generally having less than 100 nucleotides in length. An oligonucleotide may be, for example, about 75, about 50 or even less nucleotides in length.

"Transformation" means introducing DNA into an organism, i.e. a host organism, so that the DNA is replicable, either as an extrachromosomal element or by chromosomal integration.

The term "expression" and the verb "to express" denote transcription of DNA sequences and/or the translation of the transcribed mRNA in a host organism resulting in a pre-protein, i.e. not including post-translational processes.

A "promoter" is a regulatory nucleotide sequence that stimulates transcription. These terms are understood by those of skill in the art of genetic engineering and the like, for example. Like a promoter, a "promoter element" stimulates transcription but constitutes a sub-fragment of a larger promoter sequence.

The term "operably linked" refers to the association of two or more nucleic acid fragments on a single vector so that the function of one is affected by the other. For example, a promoter is operably linked with a coding sequence, i.e. a nucleotide sequence encoding a protein or a pre-protein, when it is capable of affecting the expression of that coding sequence, i.e., that the coding sequence is under the transcriptional control of the promoter.

An objective of the present invention was to provide new mutants of T7 RNA polymerase comprising no, or substantially reduced, tendency to form intramolecular disulfide bonds and generate multimers. High resolution x-ray structures of T7 RNA polymerase were carefully inspected for the identification of cysteine residues in the protein structures which may allow for introduction of mutations therein.

According to embodiments of the instant disclosure, and as disclosed herein, one or more identified cysteine residues were replaced by Serine residues. Cys-Ser substitutions were initially created as single mutations and thereafter, several different (up to six) Cys-Ser substitutions were combined in various separate coding sequences of embodiments of the T7 variants disclosed herein.

The designed T7 variants were synthesized, cloned, expressed and purified. The activity and the capability of the mutant enzymes to form multimers were examined and compared with the wild-type enzyme. It was surprisingly found that not all but only certain variants have a substantially reduced tendency to form disulfide-linked intramolecular homomultimers; that is to say, only certain T7 variants remain monomeric upon long term storage, even in the presence of oxygen, without having the requirement to be treated repeatedly with SH-reagents.

It was another surprising finding that Cys-Ser substitutions identified by the present invention do not seem to have a negative impact on RNA polymerase activity. To the contrary, Cys-Ser substitutions according to the invention can even be combined with further amino acid substitutions, e.g. with mutations which increase thermal stability of T7 RNA polymerase.

According to embodiments of the instant invention, a polypeptide comprising an improved variant of T7 RNA polymerase (T7 variant) is provided, the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference). According to some such embodiments, the improvement of the T7 variant may be attributed to the absence in aqueous solution of homomultimer formation as a result of an intermolecular disulfide bond(s), wherein at a position selected from 510 and 530 of the T7 variant, numbered from the N-terminus of the wild-type reference, a Cysteine residue is present, and wherein the T7 variant comprises one or more amino acid substitution(s) of which one (or the first) is at position 723 where Serine substitutes for the Cysteine residue (Cys723Ser).

Experimental analysis involved the introduction, at selected positions, of amino acid substitutions in the T7 polypeptide. For example, the amino acids Cysteine and Serine differ only in that the sulfur atom of the former is replaced by oxygen in the latter. However, the electronegativity of the oxygen atom provides the side chain of Serine with an increased polar effect, when compared to the SH-group containing side chain of Cysteine. As such, one or more Cys-Ser substitutions change the physico-chemicals properties of a T7 variant.

One method for protein engineering includes the modification of enzyme-encoding nucleotide sequences, but requires knowledge of the structure of an enzyme and detailed biochemical data concerning the principles underlying its function and stability. Examples of improvements in protein properties, according to embodiments of the instant disclosure, include enhanced specificity, altered substrate spectrum, and thermostability, for example.

In yet more detail, the present disclosure embodies the following items:

1. An aqueous solution in which a reducing agent with a thiol group is absent, the aqueous solution comprising a polypeptide, the polypeptide comprising a variant of T7 RNA polymerase (T7 variant), the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference),
   wherein at a position selected from 510 and 530 of the T7 variant, numbered from the N-terminus of the wild-type reference, a Cysteine residue is present,
   wherein the T7 variant comprises one or more amino acid substitution(s) of which one (or the first) is at position 723 where Serine substitutes for the Cysteine residue (Cys723Ser),
   and wherein in the aqueous solution homomultimer formation of the T7 variant as a result of one or more intermolecular disulfide bond(s) is absent.

2. The aqueous solution according to item 1, wherein in the polypeptide the number of substituted amino acids in the T7 variant is 1 to 10.

3. The aqueous solution according to item 2, wherein in the polypeptide the T7 variant further comprises a Cysteine-Serine substitution selected from the group consisting of Cys125Ser, Cys347Ser, Cys492Ser, Cys515Ser, and Cys839Ser.

4. The aqueous solution according to any of the items 2 and 3, wherein in the polypeptide the T7 variant further comprises an amino acid substitution selected from the group consisting of Val426Leu, Val426Ile, Val426Phe, Ser633Val, Ser633Met, Val650Leu, Thr654Leu, Ala702Val, and Val795Ile.

5. The aqueous solution according to item 4, wherein in the polypeptide the T7 variant comprises the amino acid substitutions Val426Leu, Val650Leu, Ala702Val, and Val795Ile.

6. The aqueous solution according to item 4, wherein in the polypeptide the T7 variant comprises the amino acid substitutions Val426Leu, Ala702Val, and Val795Ile.

7. The aqueous solution according to any of the items 1 to 6, wherein the polypeptide comprises the T7 variant and an N-terminal His-tag.

8. The aqueous solution according to any of the items 1 to 7, wherein the polypeptide comprises the T7 variant with an N-terminal Methionine.

9. A method to produce an aqueous solution with a polypeptide comprising a variant of T7 RNA polymerase (T7 variant), the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference), wherein in the aqueous solution homomultimer formation as a result of one or more intermolecular disulfide bond(s) is absent, the method comprising the steps of
   (a) providing the T7 variant by substituting in the wild-type reference Cys723, numbered from the N-terminus, with Serine (Cys723Ser);
   (b) optionally further including in the T7 variant one or more amino acid substitution(s) selected from the group consisting of Cys125Ser, Cys347Ser, Cys492Ser, Cys515Ser, and Cys839Ser;
   (c) optionally further including in the T7 variant one or more amino acid substitution(s) selected from the group consisting of Val426Leu, Val426Ile, Val426Phe, Ser633Val, Ser633Met, Val650Leu, Thr654Leu, Ala702Val, and Val795Ile;
   (d) reverse-transcribing the amino acid sequence of the polypeptide, the polypeptide comprising the T7 variant obtained in steps (a), (b), and (c), thereby obtaining a nucleotide sequence encoding the polypeptide;
   (e) expressing a nucleic acid molecule comprising the nucleotide sequence of step (d) in an expression system, and subsequently purifying the expressed polypeptide from the expression system by way of chromatography using an aqueous mobile phase in which a reducing agent with a thiol group is absent;

thereby obtaining in step (e) an aqueous solution with the polypeptide comprising the T7 variant.

10. The method according to item 9, wherein the aqueous solution obtained in step (e) is stored in the absence of a reducing agent with a thiol group.

11. The method according to any of the items 9 and 10, wherein an amount of about 1 μg to 3 μg of the purified T7 variant protein from the aqueous solution is detectably free of homomultimers as determined by SDS polyacrylamide electrophoresis and staining of the electrophoresed gel with the Simply Blue Safe Stain Kit from Invitrogen.

12. A method to synthesize a RNA molecule, comprising the steps of
    (a) providing an aqueous solution with a variant polypeptide of T7 RNA polymerase (T7 variant) according to any of the items 1 to 8;
    (b) providing a template DNA molecule comprising a T7 promoter, the T7 promoter being functionally linked to a target nucleotide sequence to be transcribed;
    (c) contacting in the aqueous solution the template DNA of step (b) with the T7 variant of step (a) in the presence of ribonucleoside triphosphates, thereby forming a reaction mixture;
    (d) incubating the reaction mixture under conditions permitting RNA polymerase activity;
    thereby synthesizing the RNA molecule.

13. A reaction mixture comprising an aqueous solution with a variant polypeptide of T7 RNA polymerase (T7 variant) according to any of the items 1 to 8, wherein the aqueous solution further comprises a template DNA molecule comprising a T7 promoter functionally linked to a target nucleotide sequence to be transcribed, and ribonucleoside triphosphates.

14. A kit comprising, in separate containers, an aqueous solution with a variant polypeptide of T7 RNA polymerase (T7 variant) according to any of the items 1 to 8 and a buffer with one or more ribonucleoside triphosphates.

15. A polypeptide comprising an improved variant of T7 RNA polymerase (T7 variant), the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference), and the improvement of the T7 variant being the absence in aqueous solution of homomultimer formation as a result of an intermolecular disulfide bond(s),
    wherein at a position selected from 510 and 530 of the T7 variant, numbered from the N-terminus of the wild-type reference, a Cysteine residue is present, and
    wherein the T7 variant comprises one or more amino acid substitution(s) of which one (or the first) is at position 723 where Serine substitutes for the Cysteine residue (Cys723Ser).

16. The polypeptide according to item 15, wherein the number of substituted amino acids in the T7 variant is 1 to 10.

17. The polypeptide according to item 16, wherein the T7 variant further comprises a Cysteine-Serine substitution selected from the group consisting of Cys125Ser, Cys347Ser, Cys492Ser, Cys515Ser, and Cys839Ser.

18. The polypeptide according to any of the items 15 to 17, wherein the aqueous solution is detectably free of homomultimers as determined by SDS polyacrylamide electrophoresis of up to about 3 μg protein (preferred about 2 μg to about 3 μg protein, more preferred up to about 2.9 μg) of the T7 variant polypeptide in purified form, and staining of the electrophoresed gel with the Simply Blue Safe Stain Kit (Invitrogen).

19. The polypeptide according to any of the items 16 to 18, wherein the T7 variant further comprises an amino acid substitution selected from the group consisting of Val426Leu, Val426Ile, Val426Phe, Ser633Val, Ser633Met, Val650Leu, Thr654Leu, Ala702Val, and Val795Ile.

20. The polypeptide according to item 19, wherein the T7 variant comprises the amino acid substitutions Val426Leu, Val650Leu, Ala702Val, and Val795Ile.

21. The polypeptide according to item 19, wherein the T7 variant comprises the amino acid substitutions Val426Leu, Ala702Val, and Val795Ile.

22. The polypeptide according to any of the items 15 to 21, wherein the polypeptide comprises the T7 variant and an N-terminal His-tag.

23. The polypeptide according to any of the items 15 to 22, wherein the polypeptide comprises the T7 variant with an N-terminal Methionine.

24. The polypeptide according to any of the items 15 to 23 in an aqueous solution.

25. The polypeptide according to item 24, wherein in the aqueous solution a reducing agent with a thiol group is absent.

26. A method to produce a polypeptide comprising an improved variant of T7 RNA polymerase (T7 variant), the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference), and the improvement of the T7 variant being the absence in aqueous solution of homomultimer formation as a result of an intermolecular disulfide bond(s), the method comprising the steps of
    (a) providing the T7 variant by substituting in the wild-type reference Cys723, numbered from the N-terminus, with Serine (Cys723Ser);
    (b) optionally further including in the T7 variant one or more amino acid substitution(s) selected from the group consisting of Cys125Ser, Cys347Ser, Cys492Ser, Cys515Ser, and Cys839Ser;
    (c) optionally further including in the T7 variant one or more amino acid substitution(s);
    (d) reverse-transcribing the amino acid sequence of the polypeptide, the polypeptide comprising the T7 variant obtained in steps (a), (b), and (c), thereby obtaining a nucleotide sequence encoding the polypeptide;
    (e) expressing a nucleic acid molecule comprising the nucleotide sequence of step (d) in an expression system, and isolating the expressed polypeptide from the expression system;
    thereby producing the polypeptide.

27. The method according to item 26, wherein in step (c) the one or more amino acid substitution(s) is/are selected from the group consisting of Val426Leu, Val426Ile, Val426Phe, Ser633Val, Ser633Met, Val650Leu, Thr654Leu, Ala702Val, and Val795Ile.

28. A method to produce a nucleic acid molecule with a nucleotide sequence encoding an improved variant of T7 RNA polymerase (T7 variant), the T7 variant having the properties of (i) DNA-dependent RNA polymerase activity, and (ii) a different composition of amino acids compared to the 883-amino acid T7 RNA polymerase polypeptide of SEQ ID NO:2 (wild-type reference), and the improvement of the T7 variant being the absence in aqueous solution of homomultimer formation as a result of an intermolecular disulfide bond(s), the method comprising the steps of
- (a) reverse transcribing an amino acid sequence of a polypeptide according to any of the items 15 to 23 or an amino acid sequence of a polypeptide obtainable by the method according to item 26 or item 27, thereby obtaining a nucleic acid sequence; followed by
- (b) synthesizing a nucleic acid molecule with the nucleic acid sequence obtained after performing step (a);

thereby producing the nucleic acid molecule encoding the T7 variant.

29. A nucleic acid molecule comprising a nucleotide sequence selected from a member of the group consisting of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and 71.

30. An expression vector comprising one or more nucleotide sequences capable of controlling transcription and/or translation and functionally linked to (a) a nucleic acid molecule obtainable by the method of item 28, or (b) a nucleic acid according to item 29.

31. A host organism capable of recombinant expression of a polypeptide, wherein the host organism is transformed with an expression vector according to item 30.

32. The host organism according to item 31, wherein the host organism is *Escherichia coli*.

33. A method to synthesize a RNA molecule, comprising the steps of
- (a) providing a variant polypeptide of T7 RNA polymerase (T7 variant) according to any of the items 15 to 23;
- (b) providing a template DNA molecule comprising a T7 promoter, the T7 promoter being functionally linked to a target nucleotide sequence to be transcribed;
- (c) contacting in aqueous solution the template DNA of step (b) with the T7 variant of step (a) in the presence of ribonucleoside triphosphates, thereby forming a reaction mixture;
- (d) incubating the reaction mixture under conditions permitting RNA polymerase activity;

thereby synthesizing the RNA molecule.

34. The method according to item 33, wherein in any of the steps (a), (b), (c), and (d) a reducing agent with a thiol group is absent.

35. The method according to item 33, wherein in any of the steps (a), (b), (c), and (d) a reducing agent selected from mercaptoethanol, dithiothreitol, dithioerythritol is absent.

36. A reaction mixture comprising in aqueous solution a template DNA molecule comprising a T7 promoter functionally linked to a target nucleotide sequence to be transcribed, ribonucleoside triphosphates, and a variant polypeptide of T7 RNA polymerase (T7 variant) according to any of the items 15 to 23, and wherein in the reaction mixture a reducing agent with a thiol group is absent.

37. A reaction mixture comprising in aqueous solution a template DNA molecule comprising a T7 promoter functionally linked to a target nucleotide sequence to be transcribed, ribonucleoside triphosphates, and a variant polypeptide of T7 RNA polymerase (T7 variant) according to any of the items 15 to 23, and wherein in the reaction mixture a reducing agent selected from mercaptoethanol, dithiothreitol, dithioerythritol is absent.

38. A kit comprising, in separate containers, a variant polypeptide of T7 RNA polymerase (T7 variant) according to any of the items 15 to 23 and a buffer with one or more ribonucleoside triphosphates, wherein the T7 variant is in aqueous solution, wherein in the aqueous solution mixture a reducing agent with a thiol group is absent.

39. A kit comprising, in separate containers, a variant polypeptide of T7 RNA polymerase (T7 variant) according to any of the items 15 to 23 and a buffer with one or more ribonucleoside triphosphates, wherein the T7 variant is in aqueous solution, wherein in the aqueous solution mixture a reducing agent selected from mercaptoethanol, dithiothreitol, dithioerythritol is absent.

40. A variant T7 RNA polymerase polypeptide having DNA-dependent RNA polymerase activity and an amino acid sequence different from SEQ ID NO.:2, the variant including a Cysteine residue at amino acid position between 510 and 530, numbered from the N-terminus of SEQ ID NO.:2, and a Serine residue substitution for the Cysteine residue at amino acid position 723, numbered from the N-terminus of SEQ ID NO.:2, wherein when in the aqueous solution the variant is devoid of homomultimer formation of intermolecular disulfide bond(s).

41. The variant of claim 40, wherein the variant comprises at least 2 and less than or equal to 10 amino acid substitutions as compared to SEQ ID NO.:2.

42. The variant of claim 40, wherein the variant further comprises a Cysteine-Serine substitution selected from the group consisting of Cys125Ser, Cys347Ser, Cys492Ser, Cys515Ser, and Cys839Ser.

43. The variant of claim 40, wherein the variant further comprises an amino acid substitution selected from the group consisting of Val426Leu, Val426Ile, Val426Phe, Ser633Val, Ser633Met, Val650Leu, Thr654Leu, Ala702Val, and Val795Ile.

44. The variant of claim 40, wherein the variant comprises amino acid substitutions Val426Leu, Val650Leu, Ala702Val, and Val795Ile.

45. The variant of claim 40, wherein the variant comprises amino acid substitutions Val426Leu, Ala702Val, and Val795Ile.

46. The variant of claim 40, wherein an N-terminal His-tag is linked to the variant.

47. The variant of claim 40, wherein an N-terminal Methionine is linked to the variant.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Example 1. Design of Amino Acid Exchange Mutations in the T7 Polypeptide

X-ray structures of T7 RNA polymerase deposited in the Protein Data Bank (http://www.wwpdb.org/pdb; codes: 1cez [referring to Cheetham, G. M. T., et al., Nature 399 (1999) 80-83], and 1s77 [referring to Yin, Y. W., and Steitz, T. A., Cell 116 (2004) 393-404]) were inspected to identify candidate sites for the introduction of mutations. To this end, cysteine residues were localized in three dimensional models and Cys residues on the surface of the T7 polypeptide which in principle could be accessible for the formation of intramolecular disulfide bonds were identified. Further, candidate amino acid residues were identified with the goal in mind to increase the stability of the protein.

Selected positions of the T7 wild-type amino acid sequence (according to SEQ ID NO:2) are shown in Table 1a which show candidate Cysteines. Table 1b provides amino acid substitution mutations expected to increase the stability of the T7 polymerase protein. The underlying rationale of the design of the mutations is also indicated, in order to increase the stability of a variant T7 polypeptide versus the wildtype reference. Thus, most of the substituting amino acids were selected either to fill hydrophobic cavities in the core or to stabilize loops located at the surface of the enzyme.

TABLE 1a

Amino Acid Mutations of T7RNA Polymerase: Design of an Enzyme with Reduced Tendency to Form Multimers Linked by Intramolecular Disulfide Bridges.

| Cys residue in WT T7 polypeptide, position in amino acid sequence (SEQ ID NO: 2) | Predicted localization | Proposed mutation |
|---|---|---|
| 125 | surface | Ser |
| 216 | buried | — |
| 271 | buried | — |
| 347 | surface | Ser |
| 467 | buried | — |
| 492 | surface | Ser |
| 510 | buried | — |
| 515 | surface | Ser |
| 530 | buried | — |
| 540 | buried | — |
| 723 | surface | Ser |
| 839 | surface | Ser |

TABLE 1b

Amino Acid Mutations of T7 RNA Polymerase: Design of an Enzyme with Increased Thermostability.

| Amino acid, WT | Position | Mutation | Rationale |
|---|---|---|---|
| Val | 426 | Leu, Ile, Phe, Trp | Fill cavity in protein core |
| Ser | 633 | Val, Leu, Met | Stabilize loop |
| Val | 650 | Leu | Stabilize loop |
| Thr | 654 | Leu | Stabilize loop |
| Ala | 702 | Val | Fill cavity in protein core |
| Val | 795 | Ile | Fill cavity in protein core |

In order to provide a coding sequence for any of the T7 mutants presented herein, the nucleotide sequence of SEQ ID NO:1 encoding the T7 wild type reference polypeptide was used as a basis. The nucleotide codons corresponding to the amino acid residues at the positions indicated in Tables 1a and 1b were mutated, in order to encode the changed amino acid at the respective position. Mutations were preferably designed in accordance with the codon usage bias of *E. coli* class II genes (as described in Hénaut, A., and Danchin, A., Analysis and Predictions from *Escherichia coli* sequences. *Escherichia coli* and *Salmonella*, Vol. 2, Ch. 114 (1996) 2047-2066, Neidhardt F C ed., ASM press, Washington, D.C.), as given in Table 2.

TABLE 2

Codon Usage in *E. Coli*.

| Amino acid | Codon | Class I | Class II | Class III | Amino acid | Codon | Class I | Class II | Class III |
|---|---|---|---|---|---|---|---|---|---|
| Phe | TTT | 55.0 9 | 29.08 | 67.14 | Leu | CTT | 9.7 | 5.56 | 19 |
|  | TTC | 44.91 | 70.92 | 32.86 |  | CTC | 10.4 | 8.03 | 9.04 |
| Leu | TTA | 10.99 | 3.44 | 20.09 |  | CTA | 3.09 | 0.83 | 6.81 |
|  | TTG | 13.02 | 5.47 | 15.05 |  | CTG | 52.79 | 76.67 | 29.99 |
| Ser | TCT | 13.26 | 32.41 | 19.63 | Pro | CCT | 13.71 | 11.23 | 28.3 |
|  | TCC | 15.02 | 26.56 | 11.34 |  | CCC | 11.19 | 1.63 | 16.26 |
|  | TCA | 10.83 | 4.79 | 22.09 |  | CCA | 18.63 | 15.25 | 31.5 |
|  | TCG | 16.88 | 7.39 | 10.6 |  | CCG | 56.47 | 71.89 | 23.94 |
| Tyr | TAT | 54.42 | 35.23 | 69.6 | His | CAT | 56.8 | 29.77 | 61.69 |
|  | TAC | 45.58 | 64.77 | 30.4 |  | CAC | 43.2 | 70.23 | 38.31 |
| Stop | TAA |  |  |  | Gln | CAA | 33.4 | 18.65 | 37.06 |
|  | TAG |  |  |  |  | CAG | 66.6 | 81.35 | 62.94 |
| Cys | TGT | 40.9 | 38.85 | 55.71 | Arg | CGT | 38.99 | 64.25 | 26.05 |
|  | TGC | 59.1 | 61.15 | 44.29 |  | CGC | 42.23 | 32.97 | 21.94 |
| Stop | TGA |  |  |  |  | CGA | 5.52 | 1.07 | 12.8 |
| Trp | TGG | 100 | 100 | 100 |  | CGG | 8.97 | 0.8 | 13.62 |
| Ile | ATT | 51.2 | 33.49 | 47.57 | Val | GTT | 23.74 | 39.77 | 34.33 |
|  | ATC | 44.37 | 65.94 | 26.65 |  | GTC | 22.48 | 13.45 | 18.95 |
|  | ATA | 4.43 | 0.57 | 25.78 |  | GTA | 14.86 | 19.97 | 21.78 |

TABLE 2-continued

Codon Usage in E. Coli.

| Amino acid | Codon | Class I | Class II | Class III | Amino acid | Codon | Class I | Class II | Class III |
|---|---|---|---|---|---|---|---|---|---|
| Met | ATG | 100 | 100 | 100 | | GTG | 38.92 | 26.81 | 24.94 |
| Thr | ACT | 14.85 | 29.08 | 26.83 | Ala | GCT | 14.52 | 27.54 | 22.86 |
| | ACC | 46.83 | 53.6 | 24.45 | | GCC | 27.62 | 16.14 | 23.67 |
| | ACA | 10.52 | 4.67 | 27.93 | | GCA | 19.63 | 24.01 | 31.27 |
| | ACG | 27.81 | 12.65 | 20.8 | | GCG | 38.23 | 32.3 | 22.19 |
| Asn | AAT | 40.87 | 17.25 | 64.06 | Asp | GAT | 62.83 | 46.05 | 70.47 |
| | AAC | 59.13 | 82.75 | 35.94 | | GAC | 37.17 | 53.95 | 29.53 |
| Lys | AAA | 75.44 | 78.55 | 72.21 | Glu | GAA | 68.33 | 75.35 | 66.25 |
| | AAG | 24.56 | 21.45 | 27.79 | | GAG | 31.67 | 24.65 | 33.75 |
| Ser | AGT | 13.96 | 4.52 | 18.73 | Gly | GGT | 32.91 | 50.84 | 31.79 |
| | AGC | 30.04 | 24.33 | 17.61 | | GGC | 43.17 | 42.83 | 24.51 |
| Arg | AGA | 1.75 | 0.62 | 15.63 | | GGA | 9.19 | 1.97 | 24.75 |
| | AGG | 1.54 | 0.29 | 9.96 | | GGG | 14.74 | 4.36 | 18.95 |

The genes which served as the basis for the data in Table 2 were clustered by using factorial correspondence analysis into three classes. Class I contains genes involved in most metabolic processes. Class II genes correspond to genes highly and continuously expressed during exponential growth. Class III genes are implicated in horizontal transfer of DNA. One can see that the distribution of codons in class III genes is more or less even, whereas it is extremely biased in class II genes (in particular, codons terminated in A are selected against).

The mutations on the codon level which were introduced in the T7 coding sequence are shown in Table 3.

TABLE 3

T7 Polymerase and Variants Thereof.

| # | T7 enzyme/variant | WT codon | Mutated codon | SEQ ID NO: |
|---|---|---|---|---|
| 1 | Wild-type | — | | 1, 2 |
| 2 | Cys125Ser | TGC | AGC | 3, 4 |
| 3 | Cys347Ser | TGT | AGC | 5, 6 |
| 4 | Cys492Ser | TGC | AGC | 7, 8 |
| 5 | Cys515Ser | TGC | AGC | 9, 10 |
| 6 | Cys723Ser | TGC | AGC | 11, 12 |
| 7 | Cys839Ser | TGT | AGC | 13, 14 |
| 8 | Cys125Ser | TGC | AGC | 15, 16 |
|   | Cys347Ser | TGT | AGC | |
|   | Cys492Ser | TGC | AGC | |
|   | Cys515Ser | TGC | AGC | |
|   | Cys723Ser | TGC | AGC | |
|   | Cys839Ser | TGT | AGC | |
| 9 | Val426Leu | GTT | CTG | 17, 18 |
| 10 | Cys723Ser | TGC | AGC | 19, 20 |
|   | Val426Leu | GTT | CTG | |
| 11 | Val426Ile | GTT | ATC | 21, 22 |
| 12 | Cys723Ser | TGC | AGC | 23, 24 |
|   | Val426Ile | GTT | ATC | |

TABLE 3-continued

T7 Polymerase and Variants Thereof.

| # | T7 enzyme/variant | WT codon | Mutated codon | SEQ ID NO: |
|---|---|---|---|---|
| 13 | Val426Phe | GTT | TTC | 25, 26 |
| 14 | Cys723Ser | TGC | AGC | 27, 28 |
|   | Val426Phe | GTT | TTC | |
| 15 | Ser633Met | TCA | ATG | 29, 30 |
| 16 | Cys723Ser | TGC | AGC | 31, 32 |
|   | Ser633Met | TCA | ATG | |
| 17 | Val650Leu | GTG | CTG | 33, 34 |
| 18 | Cys723Ser | TGC | AGC | 35, 36 |
|   | Val650Leu | GTG | CTG | |
| 19 | Thr654Leu | ACC | CTG | 37, 38 |
| 20 | Cys723Ser | TGC | AGC | 39, 40 |
|   | Thr654Leu | ACC | CTG | |
| 21 | Ala702Val | GCT | GTT | 41, 42 |
| 22 | Cys723Ser | TGC | AGC | 43, 44 |
|   | Ala702Val | GCT | GTT | |
| 23 | Val795Ile | GTA | ATC | 45, 46 |
| 24 | Cys723Ser | TGC | AGC | 47, 48 |
|   | Val795Ile | GTA | ATC | |
| 25 | Ala702Val | GCT | GTT | 49, 50 |
|   | Val795Ile | GTA | ATC | |
| 26 | Cys723Ser | TGC | AGC | 51, 52 |
|   | Ala702Val | GCT | GTT | |
|   | Val795Ile | GTA | ATC | |
| 27 | Val426Leu | GTT | CTG | 53, 54 |
|   | Ala702Val | GCT | GTT | |
| 28 | Cys723Ser | TGC | AGC | 55, 56 |
|   | Val426Leu | GTT | CTG | |
|   | Ala702Val | GCT | GTT | |

TABLE 3-continued

T7 Polymerase and Variants Thereof.

| # | T7 enzyme/ variant | WT codon | Mutated codon | SEQ ID NO: |
|---|---|---|---|---|
| 29 | Val426Leu | GTT | CTG | 57, 58 |
|    | Val795Ile | GTA | ATC |  |
| 30 | Cys723Ser | TGC | AGC | 59, 60 |
|    | Val426Leu | GTT | CTG |  |
|    | Val795Ile | GTA | ATC |  |
| 31 | Val426Leu | GTT | CTG | 61, 62 |
|    | Ala702Val | GCT | GTT |  |
|    | Val795Ile | GTA | ATC |  |
| 32 | Cys723Ser | TGC | AGC | 63, 64 |
|    | Val426Leu | GTT | CTG |  |
|    | Ala702Val | GCT | GTT |  |
|    | Val795Ile | GTA | ATC |  |
| 33 | Cys125Ser | TGC | AGC | 65, 66 |
|    | Cys347Ser | TGT | AGC |  |
|    | Cys492Ser | TGC | AGC |  |
|    | Cys515Ser | TGC | AGC |  |
|    | Cys723Ser | TGC | AGC |  |
|    | Cys839Ser | TGT | AGC |  |
|    | Val426Leu | GTT | CTG |  |
|    | Ala702Val | GCT | GTT |  |
|    | Val795Ile | GTA | ATC |  |
| 34 | Val426Leu | GTT | CTG | 67, 68 |
|    | Val650Leu | GTG | CTG |  |
|    | Ala702Val | GCT | GTT |  |
|    | Val795Ile | GTA | ATC |  |
| 35 | Cys723Ser | TGC | AGC | 69, 70 |
|    | Val426Leu | GTT | CTG |  |
|    | Val650Leu | GTG | CTG |  |
|    | Ala702Val | GCT | GTT |  |
|    | Val795Ile | GTA | ATC |  |
| 36 | Cys125Ser | TGC | AGC | 71, 72 |
|    | Cys347Ser | TGT | AGC |  |
|    | Cys492Ser | TGC | AGC |  |
|    | Cys515Ser | TGC | AGC |  |
|    | Cys723Ser | TGC | AGC |  |
|    | Cys839Ser | TGT | AGC |  |
|    | Val426Leu | GTT | CTG |  |
|    | Val650Leu | GTG | CTG |  |
|    | Ala702Val | GCT | GTT |  |
|    | Val795Ile | GTA | ATC |  |

On the amino acid level, the T7 variants are shown in the even-numbered SEQ ID NOs: 4 to 72.

The nucleotide sequences encoding the mutated T7 polypeptides which were expressed in E. coli are shown in the uneven-numbered SEQ ID NOs: 3 to 71. The nucleotide sequences are represented including the start codons for N-terminal Methionine but without any other additional artificial N-terminal structures such as His-tags.

A His-tag (in the literature also referred to as a polyHistag) is an amino acid motif in proteins that typically consists of at least six consecutive His residues (His6). While the N-terminus of a T7 variant is preferred for the addition of the His-tag, the C-terminus of the polypeptide can serve as an alternative.

For clarification, a N-terminal His-tag can be located between the Methionine at the N-terminus of the respective variant T7 polypeptide and the subsequent amino acid according to the amino acid sequence of SEQ ID NO:2, i.e. Asn. Alternatively, the His-tag can be appended to the N-terminal Methionine of the T7 variant. When appended at the C-terminus of the variant T7 polypeptide the His-tag forms the C-terminal amino acids.

The T7 variants were modified further such that each polypeptide contained a His-tag at its N-terminus to facilitate purification.

Apart from the Histidines the His-tag can additionally comprise further amino acids depending on the design of the nucleotide sequence encoding the His-tag. Thus, an oligonucleotide linker with restriction sites typically adds 1 to 5 further amino acids to the nucleotide fragment encoding the consecutive His residues in the His-tag.

The amino acid sequences of the T7 variants of Tables 1a and 1b, and the nucleic acid sequences encoding the T7 variants are shown in the sequence listing of this disclosure. No His-tags are shown as these may differ sequence-wise, depending on the particular cloning vector used. However, the differences concerning the number of Histidines and the linker sequence, according to the preferred embodiments, are not expected to have a technical impact on the T7 variants according to the invention.

Example 2. Cloning of Nucleic Acids Encoding Variants of T7 RNA Polymerase

All molecular biological procedures were performed according to standard methods (Sambrook, J., Fritsch, E. F., Maniatis, T., Molecular cloning: A Laboratory Manual second Edition, B.27 (1989) Cold Spring Harbor Laboratory Press NY (USA)). Nucleotide sequences encoding the wild-type and the mutant T7 polypeptides were synthesized by a combinatorial synthesis strategy as described (van den Brulle, J., et al., Biotechniques 45 (3) (2008) 340-343).

For expression of each of the T7 variants, the respective coding DNA sequence was cloned in appropriate expression vectors in such a way that the mutated T7 coding sequence is inserted in the right orientation under the control of an appropriate promoter, preferably an inducible promoter, particularly preferably the lac-, lacUV5-, tac- or T5 promoter. Preferred expression vectors are pUC plasmids with lac- or lacUV5 promoters or pKK plasmids. For clarification an exemplary coding sequence comprises a DNA encoding a polypeptide selected from any of SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and 71, which optionally include a further modification such as a His-tag.

The synthesized genes were cloned in plasmid pUC18. The recipient strain for transformations was E. coli XL-1 blue. Transformed clones were grown at 37° C. in LB media containing ampicillin (100 µg/ml). Plasmids were isolated and digested using EcoRI and HindIII. The resulting fragments were subjected to agarose gel electrophoresis and the respective band corresponding to the variant T7 polymerase coding sequence was extracted. The isolated fragments were ligated into the expression plasmid pKKT5 (derived from pKK177-3 [Kopetzki, E., et al., Mol. Gen. Genet. 216 (1989) 149-155] by exchanging the tac-promotors with the T5-promoter derived from the plasmid pDS [Bujard, H., et al., Methods Enzymol. 155 (1987) 416-433]) which was digested with EcoRI and HindIII.

Plasmids were transformed into E. coli UT5600 (harboring plasmid pUBS520). Clones were grown at 37° C. in LB media containing ampicillin (100 µg/ml) and kanamycin (50 µg/ml).

Example 3. Expression of Variant T7 Polymerase Polypeptides

Transformed E. coli expression strains obtained as described in Example 2 were cultivated at 37° C. in LB media containing ampicillin (100 µg/ml) and kanamycin (50 µg/ml). Induction of recombinant expression was performed at an optical density of 0.7 (measured at 578 nm) by adding IPTG in a final concentration of 1 mM. After 5 hours the cells were harvested by centrifugation and frozen at −20° C.

Example 4. Purification of Variant T7 Polymerase Polypeptides

The following purification protocol is preferred according to the invention. His6-tagged wild-type T7 polypeptide and variants of T7 RNA polymerase were routinely purified to homogeneity using chromatographic methods. Reducing additives like 2-mercaptoethanol or DTT were omitted during the entire purification process. Frozen cells (typically 2.1 g) were suspended in 30 ml lysis buffer (50 mM Tris/HCl, pH 8.0 adjusted at room temperature, 0.2 M NaCl, 2 mM EDTA). After incubation at room temperature for 15 min, the cells were sonicated. After addition of 1 ml Polymin P cell debris was removed by centrifugation at 10,000 rpm for 10 min (Eppendorf centrifuge). The supernatant was dialyzed against Buffer A (20 mM potassium phosphate, pH 7.7, 1 mM EDTA, 50 mM NaCl, 5% glycerol). After centrifugation the pool was applied on a S-Sepharose™ ff column (1.6×10 cm) at a flow rate of 5 ml/min. Elution was performed using a NaCl gradient (0 M to 1 M in Buffer A). Fractions were monitored by running aliquots on a SDS gel. Fractions containing T7 RNA polymerase were pooled. After dialysis against Buffer B (50 mM Tris/HCl, pH 8.0 (pH adjusted at 25° C.), 1 M NaCl) each enzyme solution was applied on a Ni-chelating Sepharose™ ff column (4 ml). The column was washed using Buffer B. T7 RNA polymerase was eluted in Buffer B using an imidazole gradient of 0 M to 1 M. Fractions containing the enzyme were pooled. After dialysis against storage buffer (25 mM Tris/HCl, pH 7.5 [pH adjusted at 25° C.], 10 mM NaCl, 0.1 mM EDTA) pools were stored at −20° C.

Alternative purification protocol includes the use of reducing additives (less preferred): His6-tagged wild-type T7 polymerase and T7 variants were purified separately to homogeneity using metal chelate affinity matrix chromatography. Typically, wet frozen cells (2.1 g) were suspended in 30 ml Buffer C (50 mM Tris/HCl, pH 8.1 [pH adjusted at room temperature], 1 M NaCl). To the suspension 315 µl of a lysozyme solution (10 mg/ml) were added. After incubation at room temperature for 15 min, the cells were sonicated (6×2 min). The cell debris was removed by centrifugation at 5,000 rpm for 15 min. A fraction of the supernatant (25 ml) was applied onto a Ni-chelating Sepharose column (1 ml). The column was washed using a modified Buffer C which additionally contained 10 mM imidazole. His6-tagged polypeptides were eluted in a linear gradient (10 mM-500 mM imidazole in Buffer C). Enzyme-containing fractions were pooled. After dialysis against storage buffer (10 mM potassium phosphate, 200 mM KCl, 0.1 mM EDTA, 30 mM mercaptoethanol as a reducing additive, 50% glycerol, 0.1% Tween 20, pH 7.9) the pools were stored at −20° C.

Example 5. SDS Polyacrylamide Electrophoresis (SDS-PAGE)

Samples of T7 variants were prepared according to a procedure described in Example 4. T7 RNA polymerase and variants thereof were analzed by gel electrophoresis on polyacrylamide gels containing sodium dodecylsulphate (SDS). Gradient gels (NuPAGE, 4-12%, Bis-Tris Gel, Invitrogen) were used. Typically, protein samples (0.26 mg/ml, 18 µl) were mixed with 6 µl of NuPAGE LDS (Lithium dodecyl sulfate; LDS may also be substituted by sodium dodecyl sulfate) sample buffer, (4×, Invitrogen). After heating for 2 min at 85° C., samples (20 µl) were applied on the gel. The total amount of protein in a single lane of the gel was between 1 µg and 3 µg. Gels were run in SDS Running Buffer (1×MES, Invitrogen) at 200 V for 1 hour.

Protein bands in the gels were stained using the Simply Blue Safe Stain Kit (Invitrogen product number LT6060) according to the instructions of the manufacturer. A protein molecular weight marker (Mark 12, Invitrogen) was used to determine the apparent molecular weight and to identify monomeric and homopolymeric forms of T7 RNA polymerase and/or T7 variants.

As a reference sample, commercially available T7 RNA polymerase (without His-tag) was used (wild-type T7 commercially available from Roche Applied Science, Mannheim, Germany).

Example 6. Application of Conditions for Formation of Homodimers and Higher-Order Multimers T7 enzyme and variants were purified according to Example 4 using the preferred procedure without a reducing agent. In order to compare tendencies to form intramolecular dimers and higher-order multimers, separate preparations of wild-type T7 polymerase (#1 in Table 3) and variants (##2 to 8 shown in Table 3) were incubated under conditions favoring the formation of homomultimers. To this end, samples of purified enzymes at a protein concentration of 0.2 mg/ml to 0.3 mg/ml were incubated individually at 37° C. for 16 hours in 25 mM Tris/HCl, pH 7.5 (pH adjusted at 25° C.), 0.1 mM EDTA, 100 mM NaCl under otherwise ambient conditions. This includes exposure to atmospheric oxygen.

Example 7. Analysis of Homodimer Formation

The capability to form dimers was studied for wild-type and T7 variants under stress conditions. To this end, samples were incubated in a buffer without reducing reagents. Protein monomers, dimers and higher-order multimers were determined by SDS gel electrophoresis as described in Example 5.

Samples of wild-type T7 RNA polymerase (0.2 to 0.3 mg/ml) were incubated at 37° C. for 16 hours in 25 mM Tris/HCl, pH 7.5 (adjusted at 25° C.), 0.1 mM EDTA, 100 mM NaCl. Aliquots were removed and applied on the SDS gels under reducing conditions (10 mM DTT added) or under non-reducing conditions (DTT omitted, no further reducing agent present). As shown in FIG. 1, the enzyme sample of wild-type T7 contained monomeric and dimeric forms following incubation under non-reducing conditions (in the present case without DTT, lane 1). Analysis of the sample under reducing conditions (with DTT) showed that the protein was completely transformed to the monomeric form (lane 2).

With reference to FIG. 1 (and in reference to Examples 5, 6, and 7), a stained SDS polyacrylamide gel is shown. The lanes designated M contain the Mark 12 size marker (Invitrogen). Lanes 1 and 2 contain wild-type T7 RNA polymerase. In both lanes the prominent band of fastest migrating protein represents monomeric T7 polypeptide. Samples of T7 RNA polymerase incubated for 16 h at 37° C. were treated or not treated with reducing reagents (DTT), and were subjected to electrophoresis. Lane 1: sample without DTT; Lane 2: sample treated with DTT. In lane 1 the regions marked with one and two asterisks indicate T7 multimers. The region marked with one asterisk contains only a faint smear. In the region marked with two asterisks, distinct bands can be discerned, indicating dimers and distinct higher-order homomultimers.

Further, samples of wild-type T7 and T7 variants (0.2 to 0.3 mg/ml each) were incubated at 37° C. for 16 hours in 25 mM Tris/HCl, pH 7.5 (adjusted at 25° C.), 0.1 mM EDTA, 100 mM NaCl. Aliquots were removed and applied on the SDS gels under reducing conditions or under non-reducing conditions. After incubation a sample of each treated preparation was subjected to SDS polyacrylamide gel electrophoresis as described in Example 5. Results are depicted in FIG. 2 (reducing reagents absent) and FIG. 3 (10 mM DTT added).

Figure 2:
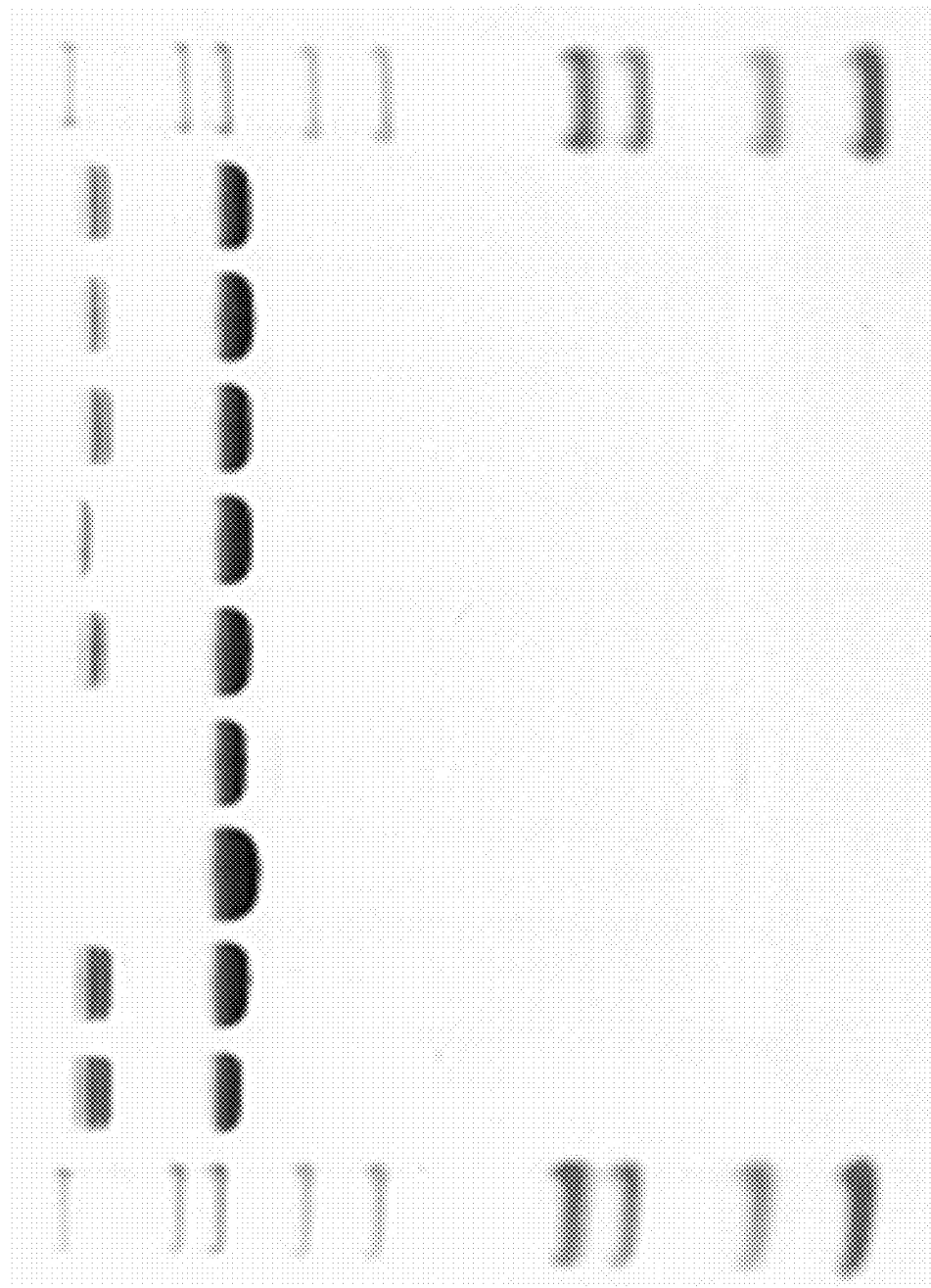
FIG. 2 is a stained SDS polyacrylamide gel (following electrophoresis) having: wild-type T7 RNA polymerase without His-tag ((Lane 1); wild-type T7 RNA polymerase including His6-tag (Lane 2); T7 variant #8 [Cys125Ser, Cys347Ser, Cys492Ser, Cys515Ser, Cys723Ser, Cys839Ser] including His6-tag (Lane 3); T7 variant #6 [Cys723Ser] including His6-tag (Lane 4); T7 variant #3 [Cys347Ser] including His6-tag (Lane 5); T7 variant #7 [Cys839Ser] including His6-tag (Lane 6); T7 variant #2 [Cys125Ser] including His6-tag (Lane 7); T7 variant #4 [Cys492Ser] including His6-tag (Lane 8); and T7 variant #5 [Cys515Ser] including His6-tag (Lane 9), in which no reducing agent was added prior to electrophoresis.

With reference to FIG. 2 (reducing reagents absent), and in reference to Examples 5, 6, and 7, a stained SDS polyacrylamide gel is shown. The lanes designated M contain the Mark 12 size marker (Invitrogen). No reducing agent was added prior to electrophoresis. Lane 1: wild-type T7 RNA polymerase without His-tag; Lane 2: wild-type T7 RNA polymerase including His6-tag; Lane 3: T7 variant #8 [Cys125Ser, Cys347Ser, Cys492Ser, Cys515Ser, Cys723Ser, Cys839Ser] including His6-tag; Lane 4: T7 variant #6 [Cys723Ser] including His6-tag; Lane 5: T7 variant #3 [Cys347Ser] including His6-tag; Lane 6: T7 variant #7 [Cys839Ser] including His6-tag; Lane 7: T7 variant #2 [Cys125Ser] including His6-tag; Lane 8: T7 variant #4 [Cys492Ser] including His6-tag; Lane 9: T7 variant #5 [Cys515Ser] including His6-tag; To varying extents homodimers and higher-order homomultimers can be seen in lanes 1, 2, 5, 6, 7, 8, and 9. Lanes 3 and 4 are detectably free of homodimers and/or homomultimers.

With reference to FIG. 3 (10 mM DTT added), and in reference to Examples 5, 6, and 7, a stained SDS polyacrylamide gel is shown. The lanes designated M contain the Mark 12 size marker (Invitrogen). 10 mM DTT was added prior to electrophoresis, to provide reducing conditions. Lane 1: wild-type T7 RNA polymerase without His-tag; Lane 2: wild-type T7 RNA polymerase including His6-tag; Lane 3: T7 variant #8 [Cys125Ser, Cys347Ser, Cys492Ser, Cys515Ser, Cys723Ser, Cys839Ser] including His6-tag; Lane 4: T7 variant #6 [Cys723Ser] including His6-tag; Lane 5: T7 variant #3 [Cys347Ser] including His6-tag; Lane 6: T7 variant #7 [Cys839Ser] including His6-tag; Lane 7: T7 variant #2 [Cys125Ser] including His6-tag; Lane 8: T7 variant #4 [Cys492Ser] including His6-tag; Lane 9: T7 variant #5 [Cys515Ser] including His6-tag.

Each lane with wild-type T7 or T7 variant in FIGS. 1, 2 and 3 represents an amount of 2.9 µg of protein.

The most surprising finding was that among the T7 variants with Cys-Ser substitutions tested, all those with a Cys723Ser mutation did not show detectable traces of homodimers or any higher-order homomultimers in SDS gels under the conditions specified in Example 5. This effect was not only observed in T7 variants with only Cys-Ser substitutions. The same effect was also obtained (i.e. homomultimers were detectably absent) when Cys723Ser was combined with any other substitution shown in Table 3. These results strongly suggest that the Cys723Ser mutation can advantageously be combined with other substitution mutations thus leading to variants with suppressed homomultimer formation.

It was noted that the effect of any other of the Cys-Ser substitution mutations selected from the group consisting of Cys125Ser, Cys347Ser, Cys492Ser, Cys515Ser, and Cys839Ser was not comparable in that homodimers or any higher-order homomultimers were detectable in varying amounts. In SDS gels T7 variants with Cys839Ser just showed a detectable reduction of homomultimer formation but no absence of homomultimers.

As shown in FIG. 1, the Cys723Ser substitution alone is remarkably effective in suppressing homodimer (and homomultimer) formation. Nevertheless, accumulating more Cys-Ser substitutions in the T7 polypeptide is desirable, in order to minimize formation of heterodimers and -multimers, i.e. to suppress covalent disulfide bonding with other proteins but T7 polypeptide. In this regard, a T7 variant comprising Cys723Ser and one or more further substitutions selected from Cys125Ser, Cys347Ser, Cys492Ser, Cys515Ser, and Cys839Ser has been found to be of great advantage.

Example 8. Analysis of DNA-Dependent RNA Polymerase Activity

A transcription-based non-radioactive assay (Method A) was used to measure the activity of purified wild-type and variants of T7 RNA polymerase obtained as described in Example 3. The enzyme activity was measured in 40 µl reaction buffer (40 mM Tris/HCl, 6 mM MgCl$_2$, 1 mM NTP (each), 0.002% [v/v] polydocanol, 4 mM spermidine, pH 8.0, 1 µg of plasmid pSPT18 cleaved (i.e. linearized) with SspI). T7 wild-type or a T7 variant polymerase enyzme was added in diluted form. After incubation at 37° C. for 30 min EDTA (0.4 M, 4 µl was added to stop the reaction.

Subsequently, each reaction mix (as an aliquot of 100 µl was mixed with 100 µl of SYBR Green II (diluted 1:4,000) and a volume of 1,890 µl 1×TE buffer were added. Fluorescence was measured photometrically (excitation wavelength: 485 nm, emission wavelength 530 nm) using a fluorimeter (Cary Eclipse, Varian). As a reference enzyme commercially available T7 RNA polymerase (Roche Applied Science, Roche Diagnostics GmbH, Mannheim) was used.

Alternatively (Method B), RNA quantification was done using Quant-iT RNA Assay (Invitrogen) on a LC480 Light Cycler platform (Roche Applied Science, Roche Diagnostics GmbH, Mannheim). As a reference enzyme commercially available T7 RNA polymerase (Roche Applied Science, Roche Diagnostics GmbH, Mannheim) was used.

To test the T7 enzyme and variants thereof under non-reducing conditions, comparative analysis was done in that in each case in a first experiment DTT was included, and in a second experiment DTT was omitted in the reaction mix.

Following incubation as described in Example 6, the enzymatic activity of samples containing protein multimers was tested, too.

Item A in Table 4 indicates the enzymatic activity of wild-type T7 polypeptide in the sample depicted in FIG. 1, lane 1 which shows the presence of dimers and higher-order multimers to a significant extent. Item B in the table corresponds to the protein in lane 2 of FIG. 1. As it becomes evident in the assay, enzymatic activity is lower in the absence of any reducing agent and increases upon addition of DTT. A comparable effect is obtained with other reducing agents with one or more thiol groups, such as mercaptoethanol or DTE.

TABLE 4

Activity of Wild-Type T7 RNA Polymerase Under Non-Reducing and Reducing Conditions.

| | Assay setup | fluorescence (arbitrary units) |
|---|---|---|
| A | no reducing agent | 8.09 |
| B | 10 mM DTT in reaction mixture | 12.43 |

The data show that the enzyme treated under non-reducing conditions shows a significantly reduced activity. This effect is directly correlated to the presence of protein dimers and higher-order multimers in the enzyme preparation.

Further, the effect of Cys-Ser substitutions in variant T7 polypeptides was determined; all assays were performed in the presence of 10 mM DTT. In each assay the concentration of the respective T7/T7 variant polymerase was 6.7 µg/ml. Table 5 shows exemplary data of wild-type and mutant T7 polypeptide enzymatic activities. T7 designations are made in accordance with those given in Table 3 above.

TABLE 5

Activity of Wild-Type T7 RNA Polymerase and Variant T7 Polypeptides.

| T7 polypeptide | fluorescence (arbitrary units) |
|---|---|
| wild-type, # 1 | 46.4 |
| T7 variant # 6 | 45.9 |
| T7 variant # 8 | 49.2 |

Very surprisingly, no negative impact with regards to enzyme activity was observed even when six substitutions, i.e. Cys125Ser, Cys347Ser, Cys492Ser, Cys515Ser, Cys723Ser, and Cys839Ser were accumulated in the same polypeptide (T7 variant #8, according to Table 3).

Example 9. Analysis of Thermostability: Half-Life Time

Further substitutions were made in the T7 polypeptide, in order to additionally enhance thermal stability of the polypeptide. T7 variants ##37 to 48 are shown in Table 6 below.

To determine the stability of wild-type T7 polymerase and T7 variants the half-life time was determined at 50° C. Samples of wild-type enzyme and purified variants (see Examples 3 and 4) were incubated in storage buffer (10 mM potassium phosphate, 200 mM KCl, 0.1 mM EDTA, 30 mM mercaptoethanol, 50% glycerol, 0.1% Tween 20, pH 7.9) at 50° C. At different time points (10, 20 and 30 min) samples were taken and the residual enzyme activity was measured as described in Example 3. The half-life time $T_{1/2}$ expressed as a number of minutes [min] means that at this time point the activity of the respective T7 variant is 50% of the activity at the time point when the experiment was started, i.e. the exposure to 50° C. was applied. Table 6 summarizes results of the measurements.

TABLE 6

Half-Life Times at 50° C. of Wild-Type T7 RNA Polymerase and T7 Variants (Single Mutations and Combination Mutations).

| # | T7 enzyme | $T_{1/2}$ [min] |
|---|---|---|
| | Reference | |
| 1 | Wild-type | 6.0-9.7 |
| | Single amino acid substitution | |
| 37 | Val426Leu | 25.0 |
| 38 | Val426Ile | 17.0 |
| 39 | Ser633Met | 13.0 |
| 40 | Val650Leu | 13.0 |
| 41 | Thr654Leu | 13.0 |
| 42 | Ala702Val | 22.0 |
| 43 | Val795Ile | 29.0 |
| | Double amino acid substitution | |
| 44 | Ala702Val Val795Ile | 22.0 |

TABLE 6-continued

Half-Life Times at 50° C. of Wild-Type T7 RNA Polymerase and T7 Variants (Single Mutations and Combination Mutations).

| # | T7 enzyme | $T_{1/2}$ [min] |
|---|---|---|
| 45 | Val426Leu Ala702Val | 39.0 |
| 46 | Val426Leu Val795Ile | 40.0 |
| | Triple amino acid substitution | |
| 47 | Val426Leu Ala702Val Val795Ile | 312.0 |
| | Quadruple amino acid substitution | |
| 48 | Val426Leu Val650Leu Ala702Val Val795Ile | 64.0 |

With regards to half-life times at 50° C., the inventors observed several surprising effects. Firstly, there were single amino acid exchanges without noticeable impact on thermostability, i.e. mutations which did not cause a substantial difference compared to the wild-type reference (#1). In this first group all T7 variants with a T1/2 value between 5 and 12 (including 5 and 12) were combined (not shown). A second group of T7 variants (not shown) was found in which the mutants had even shorter half-life times at 50° C., compared to the wild-type reference. Additionally, mutants which had lost enzymatic activity completely were combined in the second group. A third group of amino acid exchange mutations was found to enhance half-life time at 50° C. over the values found for the wild-type reference. A value greater than 12 was considered as indicating a substantial increase of thermostability in the respective T7 variant. The third group comprises the mutations according to ##37 to 48 as shown in Table 6.

Surprisingly, some amino acid substitutions which, according to theoretical predictions, were predicted to have a desired positive effect on thermostability did not lead to the expected results.

Very surprisingly, the amino acid substitutions shown in Table 6 could be combined with any of the Cys-Ser substitutions six substitutions described above, i.e. with Cys125Ser, Cys347Ser, Cys492Ser, Cys515Ser, Cys723Ser, and Cys839Ser, wherein variant T7 polypeptides with DNA-dependent RNA activity were obtained. Even more surprising, T7 variants combining (a) either Cys723Ser or all of the above six Cys-Ser substitutions with (b) a single, a double, a triple, or a quadruple amino acid substitution as shown in Table 6 were found to be more thermostable than the wild-type T7 polypeptide. Combining thermostability with a reduced tendency to form intramolecular disulfide bridges, the T7 variants ##10, 12, 14, 16, 18, 20, 22, 24, 26, 28, 30, 32, 33, 35, and 36 (according to Table 3) are particularly advantageous and very much preferred.

Example 10. Determination of Protein Concentration in Solutions

Protein concentrations were determined by measuring the optical density at 280 nm using a molar extinction coefficient of E280 nm=$1.4 \times 10^5$ $M^{-1}$ $cm^{-1}$ as described (He, B., et al., Protein Expr Purif 9 (1997) 142-151).

All publications, patents and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An aqueous solution being devoid of a reducing agent with a thiol group, the aqueous solution comprising:
a variant polypeptide of T7 RNA polymerase, the variant having DNA-dependent RNA polymerase activity and comprising the amino acid sequence of SEQ ID NO.:2, including a Cysteine residue at amino acid position between 510 and 530, numbered from the N-terminus of SEQ ID NO.:2, further having a Serine residue substitution for the Cysteine residue at amino acid position 723, numbered from the N-terminus of SEQ ID NO.:2, wherein in the aqueous solution the variant is devoid of homomultimer formation of intermolecular disulfide bond(s).

2. The aqueous solution according to claim 1, wherein the variant comprises a Cysteine-Serine substitution selected from the group consisting of Cys125Ser, Cys347Ser, Cys492Ser, Cys515Ser, and Cys839Ser.

3. The aqueous solution according to claim 1, wherein the variant further comprises an N-terminal His-tag.

4. The aqueous solution according to claim 1, wherein the variant further comprises an N-terminal Methionine.

5. The aqueous solution according to claim 1, wherein the reducing agent with the thiol group is selected from the group consisting of mercaptoethanol, dithiothreitol, dithioerythritol.

* * * * *